United States Patent [19]

Weber et al.

[11] Patent Number: 5,532,233
[45] Date of Patent: Jul. 2, 1996

[54] HETRAZEPINE COMPOUNDS WHICH HAVE USEFUL PHARMACEUTICAL UTILITY

[75] Inventors: Karl H. Weber, Gau-Algesheim; Albrecht Harreus, Ingelheim am Rhein; Werner Stransky, Gau-Algesheim; Gerhard Walther, Bingen; Jorge Casals-Stenzel, Munich; Gojko Muacevic, Ingelheim am Rhein; Hubert Heuer, Mainz; Wolf-Dietrich Bechtel, Appenheim, all of Germany

[73] Assignee: Boehringer Ingelheim KG, Ingelheim am Rhein, Germany

[21] Appl. No.: 302,578

[22] Filed: Sep. 8, 1994

Related U.S. Application Data

[63] Continuation of Ser. No. 61,392, May 13, 1993, abandoned, which is a continuation of Ser. No. 942,556, Sep. 9, 1992, abandoned, which is a continuation of Ser. No. 724,654, Jul. 2, 1991, abandoned, which is a continuation of Ser. No. 538,582, Jun. 14, 1990, abandoned, which is a continuation of Ser. No. 352,527, May 16, 1989, abandoned, which is a continuation of Ser. No. 88,758, Aug. 24, 1987, abandoned, which is a continuation of Ser. No. 76,515, Jul. 22, 1987, abandoned.

[30] Foreign Application Priority Data

Jul. 22, 1986 [DE] Germany ................. 36 24 647.62

[51] Int. Cl.$^6$ .................. C07D 495/14; A61K 31/55
[52] U.S. Cl. ............................. 514/219; 540/555
[58] Field of Search ............... 540/555; 514/219

[56] References Cited

U.S. PATENT DOCUMENTS

| | | | |
|---|---|---|---|
| 3,902,679 | 11/1975 | Nakanishi et al. | 540/555 |
| 4,621,083 | 11/1986 | Casals-Stenzel | 514/220 |

FOREIGN PATENT DOCUMENTS

| | | | |
|---|---|---|---|
| 0176927 | 4/1986 | European Pat. Off. | |
| 0194416 | 9/1986 | European Pat. Off. | |
| 2361398 | 4/1978 | France. | |
| 2386544 | 12/1978 | France. | |
| 2233457 | 2/1973 | Germany. | |
| 2508329 | 9/1975 | Germany. | |
| 2540522 | 4/1976 | Germany. | |
| 2229723 | 10/1990 | United Kingdom | 540/555 |

OTHER PUBLICATIONS

Chemical Abstract, vol. No. 79, p. No. 449, Abstract No. 66340y (1973).
Chemical Abstract, vol. No. 83, p. No. 464, Abstract No. 193276q (1975).
Chemical Abstract, vol. No. 88, p. No. 556, Abstract No. 50934v (1978).
Chemical Abstract, vol. No. 88, p. No. 576, Abstract No. 6676w (1978).
Chemical Abstract, vol. No. 88, p. No. 632, Abstract No. 22853z (1978).

*Primary Examiner*—Zinna Northington Davis
*Attorney, Agent, or Firm*—Robert P. Raymond; Wendy E. Rieder; Alan R. Stempel

[57] ABSTRACT

The invention relates to new hetrazepines of general formula

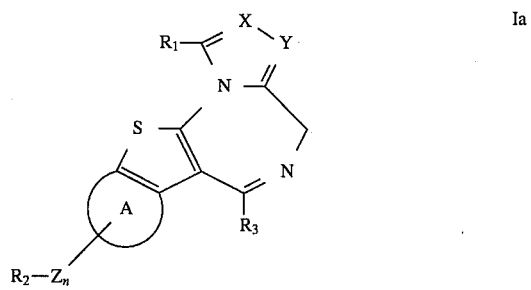

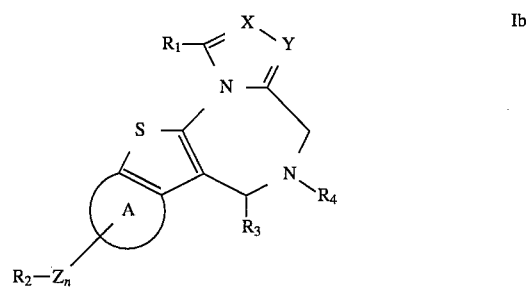

wherein
A, Z, n, X, Y, $R_1$, $R_2$, $R_3$ and $R_4$ have the meanings given in the specification.

The new compounds are intended for use in treating pathological conditions and diseases in which PAF (platelet activating factor) is implicated.

12 Claims, No Drawings

HETRAZEPINE COMPOUNDS WHICH HAVE USEFUL PHARMACEUTICAL UTILITY

This is a continuation of application Ser. No. 08/061,392, filed May 13, 1993, now abandoned, which is a continuation of application Ser. No. 942,556, filed Sep. 9, 1992, now abandoned, which is a continuation of application Ser. No. 724,654, filed Jul. 2, 1991, now abandoned, which is a continuation of application Ser. No. 538,582, filed Jun. 14, 1990, now abandoned, which is a continuation of application Ser. No. 352,527, filed May 16, 1989, now abandoned, which is continuation of application Ser. No. 088,758, filed Aug. 24, 1987, now abandoned, which is a continuation of application Ser. No. 076,515, filed Jul. 22, 1987, now abandoned.

The invention relates to new hetrazepines, the preparation thereof by known methods and their use as pharmaceutical compositions and as intermediate products.

The new hetrazepines correspond to general formula

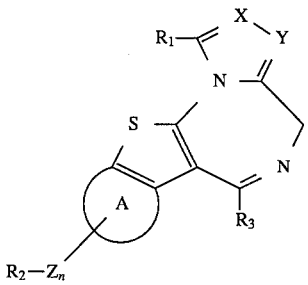

Ia

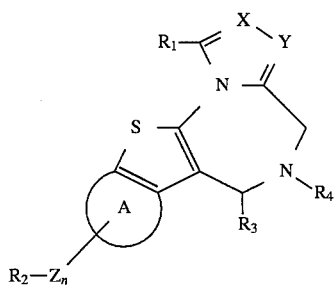

Ib wherein:

A represents a fused mono-unsaturated 5-, 6- or 7-membered ring, whilst one carbon atom may optionally be replaced by an optionally substituted nitrogen or an optionally protected carbonyl group;

Z represents a branched or unbranched alkyl or alkenyl group with n carbon atoms;

$R_1$ represents hydrogen, lower alkyl, substituted lower alkyl, cycloalkyl, lower alkoxy, substituted lower alkoxy, halogen;

$R_2$ represents hydroxy, halogen, cyano, formyl, carboxy, alkyloxycarbonyl, aryloxycarbonyl, alkyl- or aryloxycarbonylalkyloxy, alkylsulphonyloxy, arylsulphonyloxy, alkyl- or arylsulphonylamino, amino, aminocarbonyl, aminocarbonylamino, alkoxycarbonylamino, aryloxycarbonylamino, aminocarbonyloxy, an amidine, an imido group, an optionally substituted 5-, 6- or 7-membered heterocyclic ring bound via a carbon or nitrogen, benzimidazolyl, hydrogen where n>0 or hydrogen where n=0 if A contains a carbonyl function or nitrogen as a ring member, an alkyl ether, a phenyl ether, an alkylthio ether, a heterocyclic 5 or 6-membered ring linked via oxygen or sulphur, $R_3$ represents phenyl whilst the phenyl ring, preferably in the 2 position, may be mono- or polysubstituted by methyl, halogen, preferably chlorine or bromine, nitro and/or trifluoromethyl; pyridyl;

$R_4$ represents hydrogen, alkyl or alkylcarbonyl;

X, Y independently of each other represent C—$R_1$ or N but cannot both simultaneously represent C—$R_1$, or Y represents the group C—COOR' wherein R' represents alkyl or hydrogen and X represents nitrogen;

and n may represent one of the numbers 0,1,2,3,4,5 or 6, optionally in the form of their racemates, enantiomers, diastereomers and mixtures thereof; and optionally the physiologically harmless acid addition salts thereof.

Unless otherwise stated, halogen represents one of the atoms fluorine, chlorine, bromine and iodine; alkyl is a branched or unbranched alkyl group with 1 to 18 carbon atoms; lower alkyl is a branched or unbranched alkyl group with 1 to 4 carbon atoms such as methyl, ethyl, propyl, isopropyl, n-butyl, sec.-butyl, or tert.butyl; cycloalkyl is a 3 to 7-membered carbocyclic ring, such as cyclopropyl, cyclopentyl or cyclohexyl, which is optionally substituted by lower alkyl; alkyl groups may contain additional substituents and functional groups and may possibly be interrupted by heteroatoms; the term aryl is taken to mean optionally substituted aromatic groups with up to 10 carbon atoms in the ring system, the phenyl ring being preferred, whilst possible substituents include lower alkyl, cycloalkyl, lower alkoxy, hydroxy or halogen. An amino group may represent both —$NH_2$ and also mono- or disubstituted amines and also cyclic amines which may optionally contain additional substituents and also additional functional groups and heteroatoms.

Compounds of general formula I are preferred

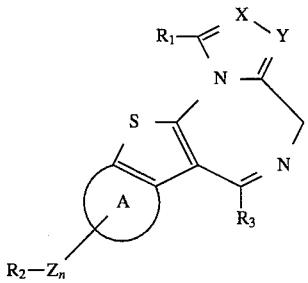

Ia

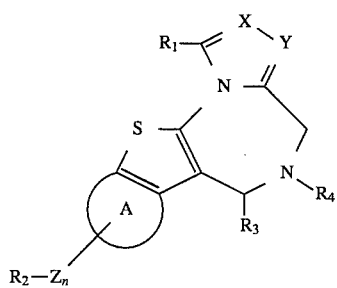

Ib wherein

A represents a fused mono-unsaturated 5, 6 or 7 membered ring whilst in the case of n=0 and $R_2$=hydrogen a carbon atom may be replaced by C=O, or A represents a fused ring of formula

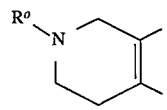

wherein $R^o$ represents a branched or unbranched alkyl group with 1 to 18, preferably 1 to 4, carbon atoms, an alkylcarbonyl or alkylthiocarbonyl group with 1 to 18, preferably 1 to 4 carbon atoms in the alkyl chain or an arylcarbonyl or arylthiocarbonyl group, an alkoxycarbonylalkyl group with up to 18, preferably up to 8, carbon atoms, an alkylcarbonylalkyl group with up to 18, preferably up to 8, carbon atoms, an alkylcarbonylaminoalkylcarbonyl group with up to 18, preferably up to 10, carbon atoms or an aminocarbonylalkyl group with up to 18, preferably up to 4, carbon atoms in the alkyl chain or hydrogen, with the proviso that if $R^o$ represents hydrogen $R_1$ cannot simultaneously represent methyl, $R_3$ cannot simultaneously represent o-chlorophenyl and X and Y cannot both represent nitrogen;

Z represents a branched or unbranched alkyl or alkenyl group with n carbon atoms;

n represents 0, 1, 2, 3, 4, 5 or 6;

X/Y independently of each other represents C—$R_1$ or N but cannot both represent C—$R_1$, or Y represents the group C—COOR' wherein R' represents alkyl or hydrogen and X represents nitrogen;

$R_1$ represents hydrogen, a branched or unbranched alkyl group with 1 to 4 carbon atoms, preferably methyl, which may optionally be substituted by hydroxy or halogen, a cyclopropyl or cyclopentyl group, a branched or unbranched alkoxy group with 1 to 4 carbon atoms, preferably methoxy, halogen, preferably chlorine or bromine;

$R_2$ represents hydroxy, amino, formyl, carboxy, cyano, branched or unbranched alkyloxycarbonyl with 1 to 18, preferably 8, carbon atoms, whilst the alkyl chain may optionally be substituted by hydroxy, amino, nitro or halogen, an optionally substituted aryloxycarbonyl group;

a group of general formula

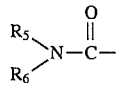

wherein $R_5$ and $R_6$ which may be identical or different represent hydrogen, a branched or unbranched alkyl, alkenyl or alkynyl group with 1 to 18 carbon atoms (which may optionally be substituted by halogen, hydroxy, nitro, amino, substituted amino, alkoxy, preferably methoxy or, if $R_6$=hydrogen or alkyl, by an ester function or by an acid amide of general formula

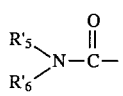

wherein R' and $R'_6$ have the same meanings as $R_5$ and $R_6$ with the exception of an acid amide) phenyl, substituted phenyl, $R_5$ or $R_6$ represent a saturated or unsaturated 5, 6 or 7 membered heterocyclic ring linked via a carbon, optionally mono or polysubstituted by branched or unbranched alkyl with 1 to 4 carbon atoms; or $R_5$ and $R_6$ together with the nitrogen atom represent a saturated or unsaturated 5, 6 or 7 membered ring optionally mono or polysubstituted by branched or unbranched alkyl groups with 1 to 4 carbon atoms, which may contain, as further heteroatoms, nitrogen, oxygen or sulphur whilst each additional nitrogen atom may be substituted by a branched or unbranched alkyl group with 1 to 4 carbon atoms, preferably methyl;

$R_2$ represents a group of general formula

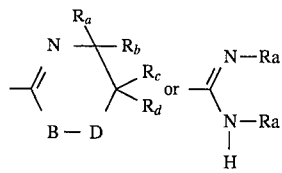

wherein

B represents oxygen, sulphur, NH or N—$C_{1-6}$alkyl,

D represents the group $(CReRf)_n$, wherein n may be 0 to 3,

Ra represents hydrogen, alkyl with 1 to 6 carbon atoms optionally substituted by a hydroxy or amino group, $C_{1-4}$ alkoxycarbonyl, dialkylaminocarbonyl, Rb, Rc, Rd, Re and Rf represent hydrogen, alkyl with 1 to 6 carbon atoms optionally substituted by a hydroxy or amino group; or phenyl;

$R_2$ represents hydrogen if A contains a carbonyl function or nitrogen as a ring member;

$R_2$ represents

$R_7$=hydrogen, $R_8$=hydrogen, alkylcarbonyl or alkoxycarbonyl with 1 to 18, preferably 1 to 6 carbon atoms, aminocarbonyl, alkylaminocarbonyl, dialkylaminocarbonyl with 1 to 18, preferably 1 to 6, carbon atoms in the alkyl chain;

$R_2$ represents hydrogen (for n>0);

$R_2$ represents halogen,

wherein $R_7$ and $R_8$, which may be identical or different, represent hydrogen, a branched or unbranched alkyl, alkenyl or alkynyl group with 1 to 18 carbon atoms which may optionally be substituted by halogen, hydroxy or a C-linked heterocyclic group, whilst the carbon chain may be interrupted by nitrogen, oxygen or sulphur, a branched or unbranched alkylcarbonyl group with 1 to 6 carbon atoms, optionally substituted by hydroxy or halogen, preferably chlorine, or substituted by an amino group (optionally mono or disubstituted by a branched or unbranched alkyl group with 1 to 6 carbon atoms) whilst the alkyl group may be substituted by halogen or hydroxy, an optionally substituted arylcarbonyl group, preferably phenylcarbonyl, an optionally substituted arylsulphonyl group, preferably phenylsulphonyl or tolylsulphonyl, an alkylsulphonyl group with 1 to 4 carbon atoms, or $R_7$ and $R_8$ together with the nitrogen atom form a saturated or unsaturated 5, 6 or 7 membered ring optionally mono- or polysubstituted by branched or unbranched alkyl groups with 1 to 4 carbon atoms, and optionally containing as further heteroatoms nitrogen, oxygen or sulphur, whilst each additional nitrogen atom may optionally be substituted by a branched or unbranched alkyl group with 1 to 4 carbon atoms, preferably methyl;

$R_2$ represents an arylsulphonyloxy group, preferably tolylsulphonyloxy or phenylsulphonyloxy, optionally mono or polysubstituted by branched or unbranched alkyl and/or alkoxy groups with 1 to 4 carbon atoms;

$R_2$ represents a branched or unbranched alkylsulphonyloxy group with 1 to 4 carbon atoms;

$R_2$ represents an arylcarbonyloxy group, preferably tolylcarbonyloxy or phenylcarbonyloxy, optionally mono or polysubstituted by branched or unbranched alkyl and/or alkoxy groups with 1 to 4 carbon atoms;

$R_2$ represents a branched or unbranched alkylcarbonyloxy group with 1 to 18, preferably 1 to 8, carbon atoms, whilst the alkyl chain may be interrupted by nitrogen, oxygen or sulphur;

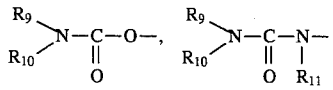

wherein $R_9$ represents hydrogen and $R_{10}$ represents an alkyl, alkenyl or alkynyl group with 1 to 4 carbon atoms, optionally substituted by halogen, an aryl group optionally mono or polysubstituted by branched or unbranched alkyl and/or alkoxy groups with 1 to 4 carbon atoms, $R_{11}$ represents hydrogen or a branched or unbranched alkyl group with 1 to 4 carbon atoms;

$R_2$ represents an imido group; a benzimidazolyl group;

$R_2$ represents a branched or unbranched alkyloxy or alkylthio group with 1 to 18, preferably 1 to 4 carbon atoms, an optionally substituted phenyloxy or phenylthio group, a saturated or unsaturated 5 or 6 membered heterocyclic ring linked via oxygen or sulphur, $R_3$ represents phenyl, wherein the phenyl ring may be mono or polysubstituted, preferably in the 2 position, by methyl, preferably halogen, preferably bromine, most particularly chlorine, nitro and/or trifluoromethyl; or pyridyl, and $R_4$ represents hydrogen, branched or unbranched alkyl with 1 to 4 carbon atoms or alkylcarbonyl with 1 to 4 carbon atoms, preferably acetyl, optionally in the form of the racemates, enantiomers, diastereomers and mixtures thereof and optionally the physiologically harmless acid addition salts thereof.

Particularly preferred compounds are compounds of general formula Ia wherein A represents a fused mono-unsaturated 5 or 6 membered ring, whilst if n=0 and $R_2$=hydrogen in a 6 membered ring a carbon atom may be replaced by CO, preferably in the 2, 3 or 4 position of the hetrazepine, or A represents a fused ring of formula

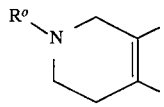

wherein $R^o$ represents acetylaminoacetyl, acetyl, thioacetyl, ethoxycarbonylmethyl, methoxycarbonylmethyl, morpholinylcarbonylmethyl or diethylaminocarbonylmethyl;

Z represents an unbranched alkyl group with n carbon atoms n represents 0, 1, 2, 3 or 4;

X/Y independently of each other represent C—$R_1$ or N, preferably both represent N or X represents C—$R_1$ and Y represents N, but they cannot both represent C—$R_1$, or Y represents C—COOR' wherein R' represents hydrogen or lower alkyl and X represents nitrogen;

$R_1$ represents hydrogen, hydroxymethyl, chloromethyl, cyclopropyl, ethyl, methoxy, ethoxy, chlorine or bromine, preferably methyl;

$R_2$ represents hydroxy, amino, carboxy, cyano, bromine, alkyloxycarbonyl with 1 to 6 carbon atoms, preferably 1 to 2 carbon atoms, a group of general formula

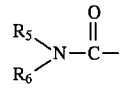

wherein $R_5$ and $R_6$, which may be identical or different, represent hydrogen, a branched or unbranched alkyl group or alkenyl group with 1 to 6, 8 or 16 carbon atoms which may optionally be substituted by halogen, hydroxy, methoxy, nitro, amino, alkylamino or dialkylamino with 1 to 4 carbon atoms in the alkyl chain, or when $R_6$=hydrogen or alkyl it may be substituted by morpholinylcarbonyl or diethylaminocarbonyl, when $R_5$=hydrogen or methyl, $R_6$ represents a thiazoline or thiazole group which may optionally be substituted by a branched or unbranched alkyl group with 1 to 4 carbon atoms, or $R_5$ and $R_6$ together with the nitrogen atom form a morpholino or piperazino group which may optionally be mono or polysubstituted by methyl;

$R_2$ represents a C-linked $\Delta^2$-imidazoline, -thiazoline, -oxazoline or tetrahydropyrimidine group which may optionally be mono or polysubstituted by alkyl with 1 to 4 carbon atoms;

$R_2$, when n=0, represents hydrogen, if A contains a carbonyl function or nitrogen as a ring member,

$R_8$ represents an alkyloxycarbonyl group with 1 to 4 carbon atoms;

when n>0

$R_2$ represents an alkylcarbonyloxy group with 1 to 3 carbon atoms;

$R_2$ represents an alkylsulphonyloxy group with 1 to 2 carbon atoms;

wherein $R_7$ and $R_8$, which may be identical or different, represent hydrogen, a branched or unbranched alkyl group with 1 to 6 carbon atoms, optionally substituted by dialkylamino with 1 to 4 carbon atoms, preferably methyl or ethyl, morpholino or N-alkylpiperazino or an indole group, an alkylcarbonyl group with 1 to 4 carbon atoms, or $R_7$ and $R_8$ together with the nitrogen atom form a morpholino or piperazino group which may optionally be mono or polysubstituted by methyl, or a triazolo group, an imidazolo group, a pyrazolo group, a pyrrolo group or an imido group, $R_2$ represents a branched or unbranched alkylsulphonyloxy group with 1 to 4 carbon atoms, preferably methylsulphonyloxy, a branched or unbranched alkylcarbonyloxy group with 1 to 8 carbon atoms, preferably 1 to 4 carbon atoms;

$R_2$ represents phenyloxy, 3,4-methylenedioxyphenoxy, a pyridinyloxy group, an alkyloxy or alkylthio group with 1 to 4 carbon atoms;

$R_3$ may represent phenyl or o-chlorophenyl, and optionally the physiologically acceptable acid addition salts thereof and their optically active compounds.

Particularly preferred compounds are those of general formula Ia wherein A represents a mono-unsaturated 5 or 6 membered ring condensed on, preferably substituted in the 3 or 4 position of the hetrazepine, Z represents an unbranched alkyl group with n carbon atoms n represents 0, 1 or 2;

X/Y both represent N, or X represents C—H or C—$CH_3$ and Y represents N;

$R_1$ represents hydrogen, cyclopropyl, methoxy, bromine, preferably methyl;

$R_2$ represents hydroxy, amino, carboxy, cyano, methoxycarbonyl, ethoxycarbonyl, a group of general formula

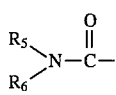

wherein $R_5$ and $R_6$, which may be identical or different, represent hydrogen, a branched or unbranched alkyl group with 1 to 6, 8 or 16 carbon atoms which may optionally be substituted by halogen, hydroxy, nitro, amino, ethylamino or diethylamino, methoxy or, if $R_6$=hydrogen or alkyl, it may be substituted by morpholinylcarbonyl or diethylaminocarbonyl, propenyl, phenyl, if $R_5$=hydrogen or methyl, $R_6$ represents a thiazoline or thiazole group which may optionally be substituted by methyl, or $R_5$ and $R_6$ together with the nitrogen atom form a morpholinyl or piperazino group which may optionally be mono or polysubstituted by methyl;

$R_2$ represents a C-linked $\Delta^2$-imidazoline, -thiazoline or -oxazoline group which may optionally be mono or polysubstituted by methyl, ethyl and/or isopropyl, a tetrahydropyrimidine ring, optionally mono or polysubstituted by methyl, a benzimidazole group, an indole group, $R_2$ when n=0 represents hydrogen, if A contains a carbonyl function or nitrogen as a ring member, or methoxycarbonylamino;

when n>0

$R_2$ represents an acetoxy group, a methanesulphonyloxy group,

wherein $R_7$ and $R_8$, which may be identical or different, represent hydrogen, a branched or unbranched alkyl group with 1 to 4 carbon atoms which may be substituted by diethylamino or morpholino, or an acetyl group or $R_7$ and $R_8$ together with the nitrogen atom form a morpholino or piperazino group which may optionally be mono or polysubstituted by methyl, or a triazolo group, an imidazolo group or a phthalimide, $R_2$ represents a branched or unbranched alkylsulphonyloxy group with 1 to 4 carbon atoms, preferably methylsulphonyloxy, a branched or unbranched alkylcarbonyloxy group with 1 to 8 carbon atoms, preferably 1 to 4 carbon atoms;

$R_2$ represents a phenyloxy group, a pyridyloxy group, 3,4-methylenedioxyphenoxy, a 1,2,4-triazol-3-yl-thio group, methoxy, $R_3$ represents phenyl, preferably o-chlorophenyl, and optionally the physiologically acceptable acid addition salts thereof, optionally the optically active compounds thereof.

Preferred imido groups are:

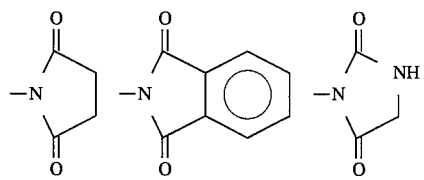

Unless otherwise stated the preferred alkyl groups and alkyl substituents on other groups are methyl, ethyl, propyl, isopropyl, n-butyl, iso-butyl and tert.-butyl.

Unless otherwise stated, the number of carbon atoms specified refers to the length of the alkyl, alkenyl or alkynyl chain without the carbonyl function.

Annealed 6-membered rings A wherein the side chain $Z_n$-$R_2$ is substituted in the 3 or 4 position of the hetrazepine or annealed 5 membered rings A wherein the side chain $Z_n$-$R_2$ is substituted in the 3 position of the hetrazepine are particularly preferred.

The new compounds of general formula Ia may be obtained by known methods from the corresponding thienodiazepine thiones of general formula II or by variation of functional groups in the side chain of the hetrazepine structural already prepared.

The new compounds of general formula Ib are obtained by reduction of compounds of general formula Ia. The reaction is carried out with known reducing agents in organic solvents, e.g. with zinc in a mixture of glacial acetic acid and an inert organic solvent, e.g. halogenated hydrocarbons such as dichloromethane, at temperatures of between ambient temperature and the boiling point of the reaction mixture or, for example, by means of lithium aluminium hydride (provided that $R_2$ is not reduced under the reaction conditions prevailing).

Compounds of general formula Ib wherein $R_4$ represents an alkyl or acyl group may be prepared from the above-mentioned compounds by alkylation or acylation using known methods.

Compounds of general formula I

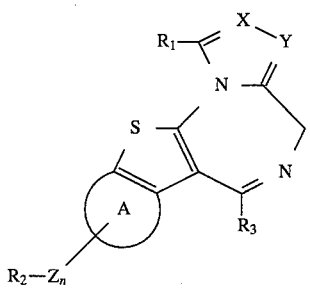

wherein $R_2$=—COOR', an ester grouping as defined hereinbefore, preferably R'=lower alkyl with 1 to 4 carbon atoms, particularly methyl or ethyl, are pharmacologically effective and are also important intermediates for the preparation of $R_2$-functionalised hetrazepines of general formula Ia or Ib.

Compounds of general formula I with a fused triazole ring may be obtained in conventional manner from the corresponding thieno-1,4-diazepine thiones of general formula

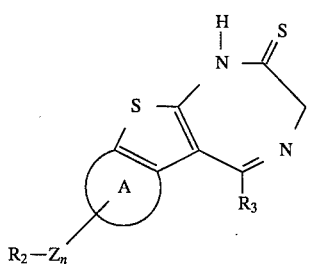

(preferably $R_2$=—COOR' (preferably R'=lower alkyl or hydrogen) or $R_2$ represents hydrogen, alkylcarbonyloxy, an ether or thioether, an acid amide or an amine).

To this end, a compound of formula II may either a) be reacted with an acid hydrazide of general formula

  III or b) be converted with hydrazine into a compound of general formula

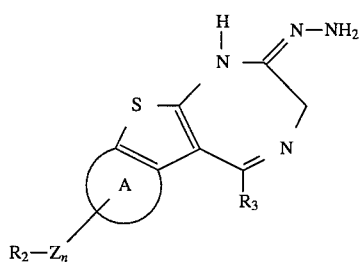  IV and subsequently being reacted with a reactive acid derivative, particularly with an acid halide, preferably an acid chloride, of general formula

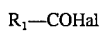  V or with an orthoester of general formula

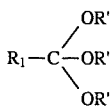  VI wherein R' represents a lower alkyl group, preferably methyl or ethyl.

The reaction of the thione II with an acid hydrazide III according to process a) is carried out in an inert organic solvent such as dioxan, dimethylformamide, tetrahydrofuran or a suitable hydrocarbon, such as benzene or toluene, at temperatures of between ambient temperature and the boiling point of the reaction mixture. The end products are isolated by known methods, e.g. by crystallisation or column chromatography.

The reaction of the thione II with hydrazine using process b) is carried out in inert organic solvents such as tetrahydrofuran, dioxan, halogenated hydrocarbons such as methylene chloride, or suitable hydrocarbons, at temperatures between ambient temperature and the boiling point of the reaction mixture.

The hydrazino-1,4-diazepines thus produced may be isolated by conventional methods or be further processed directly.

Further reaction with an acid halide V or an orthoester VI is carried out in an inert organic solvent such as a halogenated hydrocarbon or a cyclic or aliphatic ether, but may also be carried out directly in substance, appropriately with an excess of the orthoester. The end product I is isolated by known methods, for example by crystallisation.

The hetrazepines of general formula Ia wherein X represents a CH group and Y represents nitrogen are synthesised in a manner known per se from the thione of general formula II by reacting with an aminoalkyne of general formula VII wherein $R_{11}$ represents hydrogen or an alkyl group, preferably hydrogen, whilst the use of hydrochlorides for the hetrazepine cyclisation makes it possible to obtain hydrolysis-sensitive $R_2$ groups

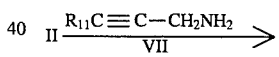

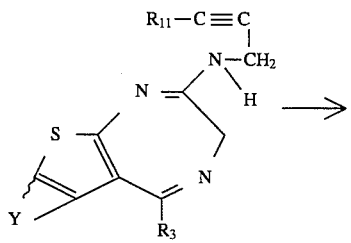

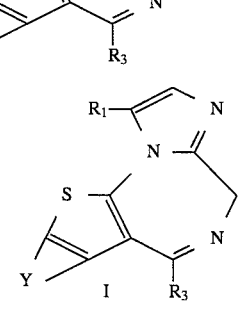

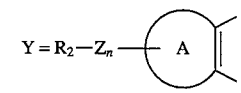

According to this process it is possible to prepare compounds of general formula I wherein $R_1$ represents an alkyl group, preferably methyl.

Another method consists in reacting the thione of general formula II with an α-amino aldehyde alkylacetal or α-aminoketone alkylketal of general formula VIII according to the following synthesis plan

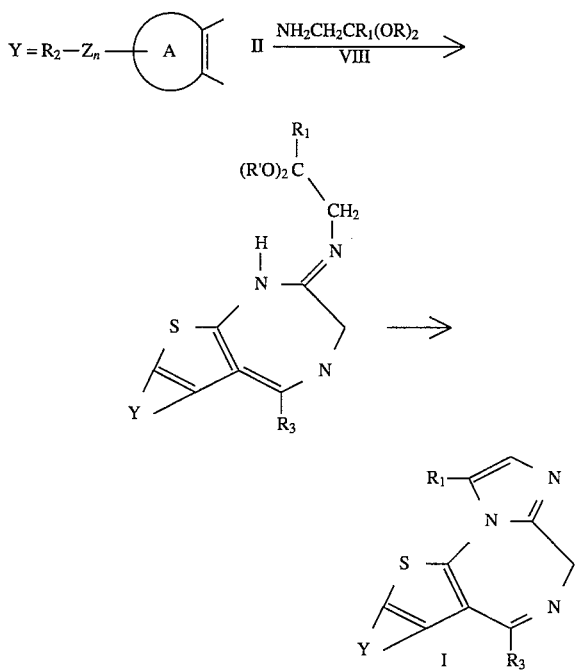

wherein $R_1$ represents hydrogen or an alkyl group with 1 to 4 carbon atoms and R' represents a lower alkyl group.

Analogous methods of synthesising an acetal or ketal of general formula VIII and an analogous method of cyclisation are described in Swiss Patent No. 580 099.

Compounds of general formula Ia wherein X represents nitrogen and Y represents CH may be obtained by decarboxylation of compounds of general formula

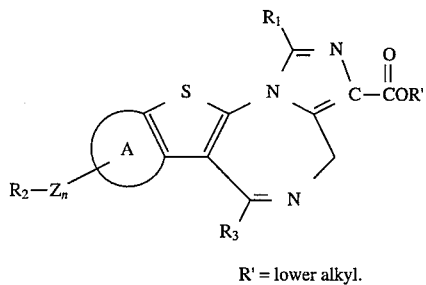

R' = lower alkyl.

Analogous methods of preparing suitable compounds of general formula Ic are described, for example, in Dutch Patent Application No. 78 03 585.

Compounds of general formula I which contain a [1,5-a] linked imidazole ring may also, for example, be prepared by methods analogous to those described in German Offenlegungsschrift 25 40 522.

Compounds of general formula I wherein $R_1$ represents chlorine or bromine are obtained from compounds wherein $R_1$=hydrogen by reacting with chlorine or bromine in pyridine.

The corresponding alkoxy compounds are obtained, for example, from one of the above-mentioned chlorine or bromine compounds by reacting with the corresponding alkoxide.

Preferably, the groups $R_1$ for halogen and alkoxy are not introduced until after the synthesis of the fully functionalised hetrazepine of general formula Ia using the method described.

The methods described above for preparing compounds of general formula I or Ia start from the thione of general formula II wherein the functional group $R_2$ is not attacked under the reaction conditions prevailing or it may be protected by suitable protecting groups. This applies particularly when $R_2$=hydrogen, a protected carbonyl function or an ester function.

Thus, diazepine thiones of general formula II may be prepared as follows.

Analogously to the process described by Gewald et al., Chem. Ber. 98, 3571 (1965) ibid 99, 94 (1966), the functionalised thienes c are obtained starting from the correspondingly functionalised cyclohexanone, cyclopentanone or cycloheptanone derivatives a by reacting with the corresponding cyanoacetophenone b. Using known methods these thienes c are converted by bromoacetylation and subsequent reaction with ammonia into the cyclised 1,4-diazepinones which are subsequently converted with phosphorous pentasulphide or Lawesson's Reagent® into the thione of general formula II.

Synthesis plan a

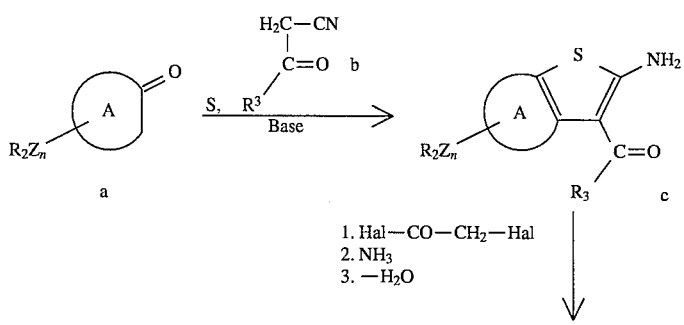

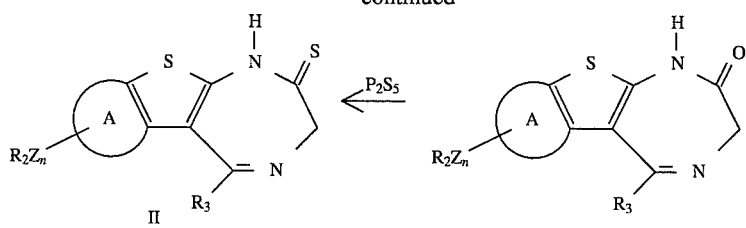

Preferably $R_2$ represents a carboxylic acid ester, such as a methyl or ethyl carboxylate or hydrogen.

The compounds of general formula c (synthesis plan a) are new and are claimed as intermediates. Compounds of this structure are valuable building blocks in the synthesis of the hetrazepines of general formula 1a and 1b.

Compounds of general formula Ia wherein A represents an unsubstituted cyclopentanone, cyclohexanone or cycloheptanone fused onto the thienodiazepine may, for example, be prepared from the 2-amino-3-benzoyl-thieno derivatives containing a carbonyl function using one of the methods described above. However, it is essential to provide the carbonyl function of the carbocyclic ring with a protecting group. Reaction plan b illustrates the principle of the reaction taking the cyclohexanone derivative as an example.

Reaction plan b:

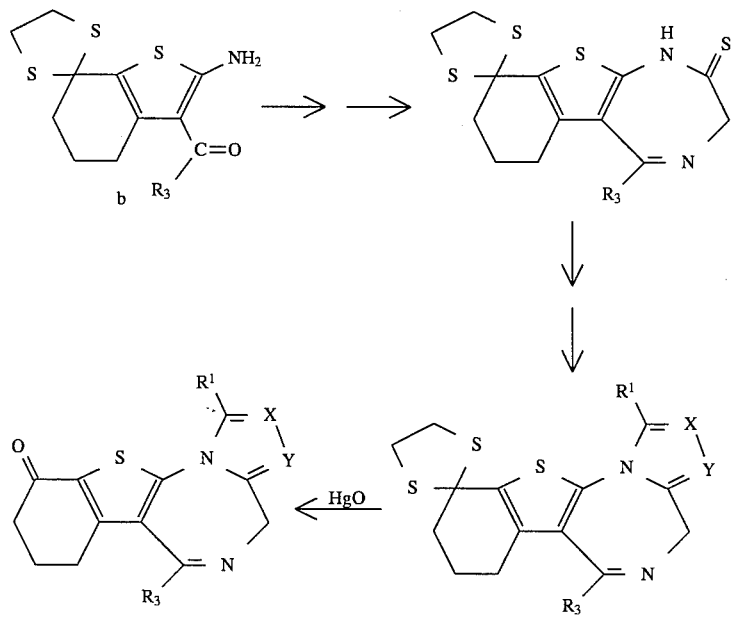

The corresponding cyclopentanone, cyclohexanone or cycloheptanone derivatives may be prepared analogously to reaction plan b. Correspondingly protected bifunctionalised cycloalkanones such as 1,4-dioxaspiro[4,5]decan-8-one for preparing the thiophene derivatives of type b using the method described by Gewald are known from the literature. The protecting groups are also introduced and cleaved by methods known from the literature.

Compounds of general formula Ia wherein A is a fused tetrahydropyrido group may be reacted, starting from N-acetylpiperidone-4 analogously to the Gewald method described above, to yield N-acetyl-hetrazepines of general formula Ia. Further functionalisation of the N-acetyl group is carried out by known methods. Compounds wherein $R^o$=hydrogen are obtained from the corresponding N-thioacetyl derivatives by saponification. Compounds of general formula Ia with the above-mentioned groups $R^o$ may be prepared from them by analogous methods.

Compounds of general formula

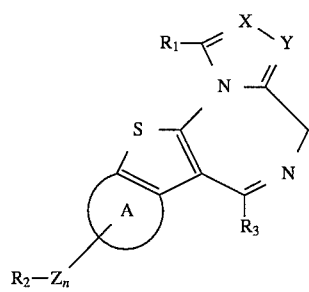

I wherein A, Z, n, $R_3$ and $R_2$ are as hereinbefore defined, $R_2$ preferably containing an ester function, are valuable starting compounds for synthesising pharmacologically active compounds and are claimed as intermediates.

The carboxylic esters of general formula Ia are valuable starting compounds for the introduction of further functional groups. Starting from the esters, the corresponding carboxylic acids of general formula Ia may be obtained by saponification, e.g. with KOH in ethanol.

Carboxylic acid amides of general formula Ia may be prepared by known methods, e.g. from the corresponding carboxylic acids or the carboxylic acid equivalents thereof by reacting with a primary or secondary amine or ammonia of general formula

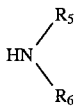

Conversion into a carboxylic acid chloride or acid anhydride or reaction of the acid in the presence of carbonyl diimidazole, sulphonyl diimidazole or cyclohexylcarbodiimide are preferred.

The reaction of the free acid with the amine is carried out in the presence of a carbodiimide, preferably cyclohexylcarbodiimide, carbonyldiimidazole or sulphonyldiimidazole in an inert solvent such as dimethylformamide, tetrahydrofuran, dioxan or halogenated hydrocarbon at temperatures of between 0° C. and the boiling point of the reaction mixture.

For the reaction of the amine with an acid halide or acid anhydride, the amine is reacted in an inert solvent, e.g. dimethylformamide, tetrahydrofuran, dioxan or a suitable hydrocarbon such as toluene, at temperatures of between ambient temperature and the boiling temperature of the reaction mixture, with the acid halide or acid anhydride, optionally with the addition of an acid binding agent such as sodium carbonate, sodium bicarbonate or a tertiary organic base, e.g. pyridine or triethylamine.

If the amine is a liquid, the reaction may also be carried out in an excess of the amine without any additional solvent.

The acid halide or acid anhydride is obtained from the free acid in conventional manner, e.g. by reacting the acid with a thionyl halide or by reacting an alkali metal salt of the acid with acetyl chloride or chloroformic acid chloride.

Instead of reacting with an amine it is also possible to react with an amino acid derivative.

Esters of general formula Ia, particularly the methyl or ethyl esters, may be converted into the corresponding alcohol by selective reduction of the ester function. The reaction is carried out with inverse addition of the reducing agent, e.g. lithium alanate or sodium borohydride (inverse activation), under generally conventional reaction conditions, e.g. in inert organic solvents, e.g. ethers or tetrahydrofuran at temperatures of between ambient temperature and the boiling temperature of the reaction mixture.

Carbamates or ureas of general formula Ia wherein $R_2=R_{10}NHCOO-$ or $R_{10}NHCONR_{11}-$ are obtained by reacting the corresponding alcohols or amines with the desired isocyanate in organic solvents, e.g. tetrahydrofuran or methylene chloride, at temperatures of between ambient temperature and the boiling point, preferably at elevated temperatures, of the reaction mixture with the addition of base, preferably DABCO (1,4-diazabicyclo(2,2,2)octane). Compounds wherein $R_2$ is alkyl- or arylcarbonyloxy are prepared from the corresponding alcohols of general formula Ia by reacting with an acid equivalent derived from a carboxylic acid of general formula

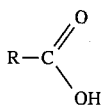

wherein R represents an aryl group or preferably a branched or unbranched alkyl group with 1 to 8 carbon atoms, whilst the carbon chain may be interrupted by nitrogen, oxygen or sulphur. The same reaction conditions may be used as for the preparation of the acid amides.

The carboxylazides may be prepared from the carboxylic acids of general formula Ia wherein $R_2$=COOH, using known methods, and these carboxylazides may then be converted into the isocyanates by Curtius rearrangement in an inert organic solvent such as dioxan. The isocyanates may be converted into urethanes and ureas by generally known methods as described above or into the primary amines by hydrolysis.

Starting from compounds of general formula Ia wherein $R_2$=OH, compounds of general formula Ia wherein $R_2$ represents an alkyl- or arylsulphonyloxy group are obtained by reacting with alkyl- or arylsulphonic acid halides. The reaction is carried out in inert organic solvents, e.g. methylene chloride, with sulphonic acid halides with the addition of acid binders such as triethylamine. The mesylates thus obtained contained the mesyl group as a good leaving group which can be exchanged nucleophilically. Correspondingly functionalised compounds of general formula Ia, e.g. $R_2=CH_3SO_3-$, may be reacted with primary or secondary amines of formula

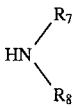

or an imido group, e.g. phthalimide. Compounds of general formula I are obtained wherein $R_2$ contains the group $NR_7R_8$ or an imido group. The reaction is carried out in inert organic solvents, e.g. tetrahydrofuran, dioxan or dimethylformamide, at between ambient temperature and the boiling point of the reaction mixture, preferably at elevated temperatures.

Starting from the mesylates of general formula I, the corresponding ethers or thioethers of general formula I are obtained by reacting the mesylates with the corresponding alcohols or mercaptanes or preferably in the form of their alkali metal salts in dioxan or dimethylformamide as solvent at a reaction temperature of between ambient temperature and the boiling point of the reaction mixture, preferably at 60°–80° C.

Compounds of general formula Ia wherein $R_2=NH_2$ are also obtained analogously to known methods by cleaving the corresponding phthalimide.

The resulting primary or secondary amines may be reacted by known methods with carboxylic acid equivalents derived from carboxylic acids of general formula

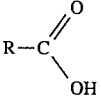

wherein R has the same meaning as $R'_5$, to yield compounds of general formula Ia wherein $R_7$ or $R_8$ represents an alkyl- or arylcarbonyl group. Oxidation of the alcohols yields the aldehydes shortened by one chain member.

Compounds of general formula Ia wherein $R_2$ represents a heterocyclic group such as an oxazoline, thiazoline, a tetrahydropyrimidine or an imidazoline, are obtained, for example, from the corresponding carboxylic acids of general formula Ia by reacting with a bifunctionalised amine such as an amino alcohol, an amino mercaptane or a diamine, in the presence of triphenylphosphine, carbon tetrachloride and a tertiary organic base in acetonitrile. The corresponding 6 and 7 membered heterocyclic groups may also be prepared analogously. The reaction is carried out in a temperature range from 0° C. to the boiling point of the reaction mixture, preferably from 0° C. to ambient temperature. Compounds of general formula Ia wherein $R_2$ represents an oxazoline group are also obtained from the correspondingly hydroxy-functionalised carboxylic acid amides by a cyclisation reaction with thionyl chloride in an inert organic solvent such as methylene chloride. These may, if desired, be converted into the corresponding thiazoline by sulphurisation, e.g. with phosphorous pentasulphide or Lawesson's Reagent®.

Compounds of general formula I wherein $R_2$ represents an amidine having the structure

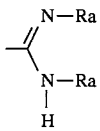

are obtained analogously to the method described above from the corresponding carboxylic acid and a primary amine.

Compounds of general formula Ia wherein $R_2$ is a cyano group are obtained from the corresponding primary carboxylic amides by reacting with phosphorous oxychloride in an inert organic solvent, e.g. dichloroethane, under reflux conditions or by reacting the corresponding bromide with triethyl ammonium cyanide, for example, preferably at room temperature.

Compounds of general formula Ia wherein $R_2$ is an imidazolidine optionally substituted by branched or unbranched alkyl groups, may be obtained starting from compounds Ia wherein $R_2$=CN via the imidoethylester hydrochloride by reacting with a diamine (Pinner reaction). The imidoethylester hydrochloride is formed by treating the nitrile with an excess of ethanolic hydrochloric acid. The crude crystalline product obtained is reacted in ethanol with the diamine (e.g. ethylene diamine) first while cooling with ice and then under reflux conditions. In this way, compounds of formula Ia are obtained wherein $R_2$ is an imidazoline-2 group. The amino function may be alkylated by known methods in the case of N—H.

Compounds of general formula Ia wherein $R_2$ is a halogen atom, e.g. iodine, are obtained from a compound of general formula Ia wherein $R_2$ is a toluenesulphonic acid group by reacting with a corresponding halogenating agent, e.g. NaI, in anhydrous solvents, e.g. acetone.

Compounds of general formula Ia wherein A represents

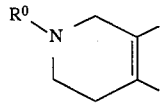

and $R^0$ is alkyl, substituted methyl, alkylcarbonyl, substituted alkylcarbonyl or arylcarbonyl are obtained by alkylation or acylation of compounds of general formula I wherein $R^0$=hydrogen, whilst the corresponding thiocarbonyl compounds are obtained by reacting the carbonyl compound with a sulphur reagent, e.g. phosphorous pentasulphide or Lawesson's Reagent®.

If the compounds according to the invention have an asymmetrically substituted carbon atom they may be resolved into their optically active enantiomers by known methods, e.g. by chromatography on optically active column material.

The following compounds, for example, are prepared by known analogous methods or analogously to the methods described.

4-(Morpholin-4-yl-carbonyl)-6-(2-chlorophenyl)-11-methyl-2,3,4,5-tetrahydro-8H-[1]benzothieno[3,2-f][1,2,4]triazolo[4,3-a][1,4]diazepine 3-(Morpholin-4-yl-carbonyl)-6-(2-chlorophenyl)-11-methyl-2,3,4,5-tetrahydro-8H-[1]benzothieno[3,2-f][1,2,4]triazolo[4,3-a][1,4]diazepine 3-(N,N-Diethylaminocarbonyl)-6-(2-chlorophenyl)-11-methyl-2,3,4,5-tetrahydro-8H-[1]benzothieno[3,2-f][1,2,4]triazolo[4,3-a][1,4]diazepine 4-(N,N-Diethylaminocarbonyl)-6-(2-chlorophenyl)-11-methyl-2,3,4,5-tetrahydro-8H-[1]benzothieno[3,2-f][1,2,4]triazolo[4,3-a][1,4]diazepine 4-(4-Methylpiperazinylcarbonyl)-6-(2-chlorophenyl)-11-methyl-2,3,4,5-tetrahydro-8H-[1]benzothieno[3,2-f][1,2,4]triazolo[4,3-a][1,4]diazepine 4-(N-Methyl-N-2-hydroxyethylaminocarbonyl)-6-(2-chlorophenyl)-11-methyl-2,3,4,5-tetrahydro-8H-[1]benzothieno[3,2-f][1,2,4]triazolo[4,3-a][1,4]diazepine 4-(N,N-Dimethylaminocarbonyl)-5-(2-chlorophenyl)-10-methyl-3,4-dihydro-2H,7H-cyclopenta[4,5]thieno[3,2-f][1,2,4]triazolo[4,3-a][1,4]diazepine 3-(N,N-Diethylaminocarbonyl-5-(2-chlorophenyl)-10-methyl-3,4-dihydro-2H,7H-cyclopenta[4,5]thieno[3,2-f][1,2,4]triazolo[4,3-a][1,4]diazepine 3-(N,N-Diethylaminocarbonyl-5-(2-chlorophenyl)-10-bromo-3,4-dihydro-2H,7H-cyclopenta[4,5]thieno[3,2-f][1,2,4]triazolo[4,3-a][1,4]diazepine 4-(Morpholin-4-yl-carbonylmethylaminocarbonyl)-5-(2-chlorophenyl)-10-bromo-3,4-dihydro-2H,7 H-cyclopenta[4,5]thieno[3,2-f][1,2,4]triazolo[4,3-a][1,4]diazepine 4-(Morpholin-4-yl-carbonyl)-6-(2-chlorophenyl)-11-methyl-2,3,4,5-tetrahydro-8H-[1]benzothieno[3,2-f]imidazo[1,2-a][1,4]diazepine 4-(N,N-Diethylamino)-6-(2-chlorophenyl)-11-methyl-2,3,4,5-tetrahydro-8H-[1]benzothieno[3,2-f]imidazo[1,2-a][1,4]diazepine 3-(N-Morpholinomethyl)-5-(2-chlorophenyl)-10-methyl-3,4-dihydro-2H,7H-cyclopenta[4,5]thieno[3,2-f][1,2,4]triazolo[4,3-a][1,4]diazepine 3-(Acetoxymethyl)-5-(2-chlorophenyl)-10-methyl-3,4-dihydro-2H,7H-cyclopenta[4,5]thieno[3,2-f][1,2,4]triazolo-[4,3-a][1,4]diazepine 3-(1,2,4-Triazol-1-yl-methyl)-5-(2-chlorophenyl)-10-methyl-3,4-dihydro-2H,7 H-cyclopenta[4,5]thieno[3,2-f][1,2,4]triazolo-[4,3-a][1,4]diazepine 3-(N-2,6-Dimethylmorpholino-methyl)-5-(2-chlorophenyl)-10-methyl-3,4-dihydro-2H,7 H-cyclopenta[4,5]thieno[3,2-f][1,2,4]triazolo-[4,3-a][1,4]diazepine 3-Acetoxymethyl-5-(2-chlorophenyl)-3,4-dihydro-2H,7H-cyclopenta[4,5]thieno[3,2-f][1,2,4]triazolo[4,3-a][1,4]diazepine 4-Acetoxymethyl-6-(2-chlorophenyl)-11-methyl-2,3,4,5-tetrahydro-8H-cyclohexa-[4,5]thieno[3,2-f]imidazo[1,2-a][1,4]diazepine 3-Acetoxymethyl-5-(2-chlorophenyl)-10-methyl-3,4-dihydro-2H,7H-cyclopenta[4,5]thieno[3,2-f]imidazo[1,2-a][1,4]diazepine 3-Diethylaminomethyl-5-(2-chlorophenyl)-10-methyl-3,4-dihydro-2H,7H-cyclopenta[4,5]thieno[3,2-f][1,2,4]triazolo[4,3-a][1,4]diazepine 4-Hydroxymethyl-6-(2-chlorophenyl)-11-methyl-2,3,4,5-tetrahydro-8H-[1]benzothieno[3,2-f][1,2,4]triazolo[4,3-a][1,4]diazepine 4-(N-Morpholinomethyl)-6-(2-chlorophenyl)-11-methyl-2,3,4,5-tetrahydro-8H-[1]benzothieno[3,2-f][1,2,4]triazolo[4,3-a][1,4]diazepine 4-(Pyrazol-1-yl-methyl)-6-(2-chlorophenyl)-2,3,4,5-tetrahydro-8H-[1]benzothieno[3,2-f][1,2,4]triazolo[4,3-a][1,4]diazepine 4-[4,4-Dimethyl-2-oxazolin-2-yl]-6-(2-chlorophenyl)-11-methyl-2,3,4,5-tetrahydro- 8H-[1]benzothieno[3,2-f][1,2,4]triazolo[4,3-a][1,4]diazepine 4-[4,4-Dimethyl-2-imidazolin-2-yl]-6-(2-chlorophenyl)-11-methyl-2,3,4,5-tetrahydro- 8H-[1]benzothieno[3,2-f][1,2,4]triazolo[4,3-a][1,4]diazepine 4-[1,4,4-Trimethyl-2-imidazolin-2-yl]-6-(2-chlorophenyl)-11-methyl- 2,3,4,5-tetrahydro-8H-[1]benzothieno[3,2-f][1,2,4]triazolo[4,3-a][1,4]diazepine 4-Aminocarbonyl-6-(2-chlorophenyl)-11-methyl-2,3,4,5-tetrahydro-8H-[1]benzothieno[3,2-f][1,2,4]triazolo[4,3-a][1,4]diazepine 4-[Morpholin-4-yl-carbonyl]-6-(2-chlorophenyl)-2,3,4,5-tetrahydro-8H-[1]benzothieno[3,2-f]imidazo[1,5-a][1,4]diazepine 4-[4,4-Dimethyl-2-thiazolin-2-yl]-6-(2-chlorophenyl)-11-methyl-2,3,4,5-tetrahydro- 8H-[1]benzothieno[3,2-f][1,2,4]triazolo[4,3-a][1,4]diazepine 4-Amino-6-(2-chlorophenyl)-11-methyl-2,3,4,5-tetrahydro-8H-[1]benzothieno[3,2-f][1,2,4]triazolo[4,3-a][1,4]diazepine 3-(N-Morpholinyl-methyl)-5-(2-chlorophenyl)-10-methyl-3,4-dihydro-2H,7H-cyclopenta[4,5]thieno[3,2-f]imidazo[1,2-a][1,4]diazepine 4-(1,2,4-Triazol-1-yl-methyl)-6-(2-chlorophenyl)-11-methyl-2,3,4,5-tetrahydro-8H-[1]benzothieno[3,2-f][1,2,4]triazolo[4,3-a][1,4]diazepine 4-(1,2,4-Triazol-1-yl-methyl)-6-(2-chlorophenyl)-11-methyl-2,3,4,5-tetrahydro-8H-[1]benzothieno[3,2-f]imidazo[1,2-a][1,4]diazepine.

The compounds according to the invention have a PAF-antagonistic activity. As is well known, PAF (platelet activating factor) is the phospholipid acetyl-glyceryl-ether-phosphoryl-choline (AGEPC) which is known as a potent lipid mediator released by animal and human proinflammatory cells. These cells include primarily basophilic and neutrophilic granulocytes, macrophages (from blood and tissue) and thrombocytes which are involved in inflammatory reactions.

In pharmacological trials, PAF is seen to cause bronchoconstriction, a lowering of blood pressure, the triggering of thrombocyte aggregation and a proinflammatory activity. These experimentally demonstrable effects of PAF indicate, directly or indirectly, possible functions of this mediator in anaphylaxis, in the pathophysiology of bronchial asthma and in inflammations in general.

PAF antagonists are needed on the one hand in order to clarify any additional pathophysiological functions of this mediator in animals and humans and on the other hand in order to treat pathological conditions and diseases in which PAF is implicated. Examples of indications for a PAF antagonist include inflammatory processes of the tracheobronchial tree (acute and chronic bronchitis, bronchial asthma) or of the kidneys (glomerulonepthritis), the joints (rheumatic complaints), anaphylactic conditions, allergies and inflammation in the mucous membranes and the skin (e.g. psoriasis) and shock caused by sepsis, endotoxins or burns. Other important indications for a PAF antagonist include lesions and inflammation in the gastric and intestinal linings, such as gastritis, and peptic ulcers in general, but particularly ventricular and duodenal ulcers.

The compounds according to the invention are also suitable for treating the following conditions: obstructive lung diseases such as bronchial hyperreactivity, inflammatory diseases of the pulmonary passages, such as chronic bronchitis; cardiac/circulatory diseases such as polytrauma, anaphylaxis, arteriosclerosis, inflammatory intestinal diseases, EPH gestosis (edema-proteinuria hypertension), diseases of extracorporeal circulation, ischaemic diseases, inflammatory and immunological diseases, immune modulation in the transplanting of foreign tissues, immune modulation in leukaemia; propagation of metastasis, e.g. in bronchial neoplasia, diseases of the CNS, such as migraine, agarophobia (panic disorder), and the compounds according to the invention have also proved effective cyto- and organoprotective agents, e.g. for neuroprotection, e.g. in cirrhosis of the liver, DIC (disseminated intravascular coagulation); side effects of drug therapy, e.g. anaphylactoid circulatory reactions, incidence caused by contrast media, side effects in tumour therapy; incompatibilities in blood transfusions; fulminant liver failure ($CCl_4$ intoxication) amanita phalloides intoxication (mushroom poisoning); symptoms of parasitic diseases (e.g. worms).

Additional indications are immune regulation in case of aids, diabetes, juvenile diabetes, diabetic retinopathy, polytrauma, hemorrhagic shock, CNS: ishemia, multiple sclerosis.

PAF-associated interaction with tissue hormone (autocoid hormones), lymphokines and other mediators.

The PAF-antagonistic activity of individual benzodiazepines is known, cf. E. Kornecki et al., Science 226, 1454–1456 (1984). Alprazolam has an $IC_{50}$ (concentration for a 50% inhibition of aggregation) of 14 μM and triazolam has an $IC_{50}$ of 9 μM using the method described. These compounds which have been proven as tranquillisers and hypnotics and which are commercially available are, however, unsuitable in many cases for use as PAF antagonists in therapy, owing to their marked sedative activity, despite their relatively good PAF-antagonistic activity.

The compounds according to the invention, on the other hand, have no sedative activity, whilst the PAF antagonist activity is at least equivalent to that of the known benzodiazepines.

The PAF-antagonistic activity of some compounds of formulae Ia and Ib was tested in vitro on the inhibition of blood platelet aggregation.

1. Tests in vitro: inhibition of blood platelet aggregation

The PAF-induced aggregation of human thrombocytes in vitro was used to determine the PAF antagonistic activity of substances. In order to obtain thrombocyte-rich plasma (TRP) blood is taken from an uncongested vein using a plastic syringe which contains 3.8% sodium citrate solution. The ratio of sodium citrate solution to blood is 1:9. After careful mixing the citrated blood is centrifuged for 20 minutes at 150×g (1200 rpm). The thrombocyte aggregation is measured using the method developed by Born and Cross (G. V. R. Born and M. J. Cross, J. Physiol. 168, 178 (1963)), with PAF being added to the TRP with constant stirring to initiate aggregation.

The test substance is added in a volume of 10 μl 2–3 minutes before aggregation is initiated. The solvent used is either distilled water, ethanol and/or dimethyl sulphoxide. Control mixtures are given corresponding volumes of these solvents. After the initial absorption has been recorded (2–3 minutes) aggregation is induced with PAF ($5×10^{-8}$M).

The peak of the first aggregation wave is used in order to assess the effects of the substance. The PAF-induced maximum absorption rate (=maximum aggregation×100%) is tested at the same time in a parallel mixture (=control mixture in one of the channels of the 2-channel aggregometer) to each test mixture (second channel) and used as a 100% value. The aggregation value achieved under the influence of the test substance is given as 100%.

Each test substance is tested at concentrations of from $10^{-3}$ to $10^{-8}$ M with a random sampling scope of n=4 to determine any inhibitory activity on the PAF-induced thrombocyte aggregation. A concentration-activity curve is then drawn up from 3 concentrations and the $IC_{50}$ is determined (concentration for a 50% inhibition of aggregation). With some compounds, only approximate tests for guidance are carried out.

The PAF-antagonistic activity of 6-(2-chlorophenyl)-11-methyl- 2,3,4,5-tetrahydro-8H-[1]benzothieno[3,2-f][1,2,4]triazolo[4,3-a][1,4]diazepine (A) and 6-(2-chlorophenyl)-11-methyl-2,3,4,5-tetrahydro- 8-H-pyrido[4',3':4,5]thieno-[3,2-f][1,2,4]triazolo[4,3-a][1,4]diazepine (B) is known from European Patent Application No. 176 927.

These compounds are found to have $IC_{50}$ values (the concentration at which a 50% inhibition of aggregation is measured) of 2.5 (A) and 10 (B).

In the benzodiazepine receptor bonding test using [$^3$H] flunitrazepam as radioligand (Bechtel et al in Arzneimittel-forschung 3a, 1986, 534), the two compounds are found to have values of 21 (A) and 35 (B) ($10^{-9}$ mol), indicating that these compounds have a central activity. Surprisingly, it has now been found that some of the compounds of general formula Ia according to the invention show substantially greater values in the flunitrazepam bonding test and are no longer CNS-active.

The following Table lists the "PAF values" and the values for the flunitrazepam bonding test of some known compounds and also some compounds according to the invention (unless otherwise noted the racemate was tested):

TABLE A

| Compound | $IC_{50}$ value PAF $10^{-6}$ | $IC_{50}$ value FNB $10^{-9}$ Mol |
|---|---|---|
| Alprazolam | 14 | 5.5 |
| Triazolam | 9 | 1.4 |
| Compound (A) | <2.5 | 21 |
| Compound (B) | <7 | 35 |
| Example 1 | 0.5 | >5000 |
| Example 2 | 2.5 | >5000 |
| Example 7 | 0.3 | 3600 |
| Example 10 | 0.3 | — |
| Example 11 | 0.5 | 5000 |
| Example 17 | 1.8 | 1070 |
| Example 18 | 1.3 | — |
| Example 19 | 0.6 | — |
| Example 21 | 0.3 | >5000 |
| Example 25 | 1 | 2300 |
| Example 33 | 2.3 | — |
| Example 35 | 3.3 | >5000 |
| Example 36 | 0.4 | >5000 |
| Example 37 | 1.8 | >5000 |
| Example 38 | 2.7 | — |
| Example 46 | 4.8 | 1460 |
| Example 58 | 0.4 | 380 |
| Example 62 | 0.4 | 4600 |
| Example 63 | 0.4 | >5000 |
| Example 64 | 0.8 | — |

TABLE A-continued

| Compound | $IC_{50}$ value PAF $10^{-6}$ | $IC_{50}$ value FNB $10^{-9}$ Mol |
|---|---|---|
| Example 68 | 0.4 | — |
| Example 79 | 2.2 | 4800 |
| Example 83 | 0.9 | — |
| Example 86 | 1 | >5000 |
| Example 66 | <0.2 | 920 |
| Example 113 | <0.2 | 3000 |

2. In vivo tests 2.1. Antagonisation of the PAF-induced bronchoconstriction in anaesthetised guinea pigs Spontaneously breathing male guinea pigs weighing 300 to 450 g are orally given the test substance for a control carrier 1 hour before the intravenous infusion of PAF (30 ng/(kg×min). The test animals are then anaesthetised by intraperitoneal route with 2 mg/kg of urethane, after which the jugular vein, carotid artery and trachea are cannulated. In the control animals the PAF infusion induces a powerful and long-lasting bronchoconstriction which is measured by means of the volume of breath, compliance and resistance, and also a lowering of blood pressure. After about 7 to 10 minutes the animal dies. With the PAF antagonists described, these effects on breathing and blood pressure and the onset of death can be prevented.

2.2. Antagonisation of the PAF-induced lowering of blood pressure in the anaesthetised rat Male Wistar rats weighing 200 to 250 g with normal blood pressure are anaesthetised by intraperitoneal route with 2 mg/kg of urethane. The carotid artery and jugular vein are cannulated. An intravenous PAF infusion (30 ng/(kg×min)) induces a sharp and long-lasting fall in blood pressure in the control animals. This can be reversed, depending on dosage, by intravenous injections (cumulative administration) of the compounds described. Oral or intravenous administration of the compound before the PAF infusion starts can also prevent the lowering of blood pressure by the above-mentioned PAF infusion, depending on dosage.

2.3. Antagonisation of the PAF-induced skin wheals in the rat (modified according to P. P. Koelzer and K. H. Wehr, Arzneim.-Forsch. 8, 181 (1958)

Intracutaneous injection of PAF induces skin wheals which indicate the PAF-induced increase in the permeability of the blood vessels.

Male Wistar rats with a body weight of 250±20 g are shaved over their abdomens. Then 1 ml/kg of a 1% trypan blue solution is injected through a vein in the animal's tail. Intracutaneous injections of physiological saline solution or PAF solution (12.5 to 15.0 ng per site in 0.1 ml) are administered symmetrically with respect to the centre line (linea alba) at three sites at intervals of about 1.5 cm. Whereas no reaction was observed at the injection site of the saline solution, PAF caused a skin reaction (wheal) which was made visible by blue coloration of varying intensity, depending on the dose of PAF. By simultaneous intracutaneous administration of the compounds described or by intravenous pre-treatment this PAF-induced skin reaction could be prevented.

3. Effects on the central nervous system

It is generally known that substances of this type of structure have central nervous effects which are undesirable for a compound with a PAF-antagonistic activity. Therefore, the compounds described were tested for their hypnogenic and anti-convulsive activities and their effects on locomotion. Possible hypnotic effects were investigated on guinea pigs weighing from 400 to 450 g. Doses of up to 200 mg/kg p.o. of these substances were incapable of causing a hypnotic or sedative effect in these animals.

In order to investigate any anti-convulsive activity it is possible to use pentetrazole antagonism in mice (20 to 25 g body weight) (M. I. Gluckmann, Current Therapeutic Research, 7:721, 1965). In this test, doses of up to 100 mg/kg p.o. of these compounds (administered 1 hour before the pentetrazole) showed no influence on the mortality caused by pentetrazole (125 mg/kg j.p., LD 100). The effect on night motility (locomotion) in mice (body weight 20 to 25 g) can be investigated using a light beam cage. The number of times the light beam is broken is recorded. Doses of up to 300 mg/kg p.o. of the above-mentioned compounds showed no activity.

The new compounds of general formulae Ia and Ib may be administered by topical, oral, transdermal or parenteral route or by inhalation. The compounds are present as active ingredients in conventional pharmaceutical forms, e.g. in compositions consisting essentially of an inert pharmaceutical carrier and an effective dose of the active substance, such as plain or coated tablets, capsules, lozenges, powders, solutions, suspensions, inhalation aerosols, ointments, emulsions, syrups, suppositories, etc. An effective dose of the compounds according to the invention is between 1 and 50, preferably between 3 and 20 mg/dose for oral administration, and between 0.001 and 50, preferably between 0.1 and 10 mg/dose for intravenous or intramuscular use. For inhalation, solutions containing 0.01 to 1.0, preferably 0.1 to 0.5% of active substance should be used.

EXAMPLE 1

4-(Morpholin-4-yl-carbonyl)-6-(2-chlorophenyl)-11-methyl-2,3,4,5-tetrahydro-8H-[1]benzothieno[3,2-f][1,2,4]triazolo[4,3-a][1,4]diazepine 10 g (0.024 mol) of 4-Carboxyl-6-(2-chlorophenyl)-11-methyl- 2,3,4,5-tetrahydro-8H-[1]benzothieno[3,2-f][1,2,4]triazolo[4,3-a]diazepine are mixed with 4.2 g (0.026 mol) of carbonyl diimidazole in 60 ml of methylene chloride and stirred for 45 minutes at ambient temperature. After the addition of 2.2 g (0.025 mol) of morpholine stirring is continued for a further 4 hours. The reaction mixture is then washed with saturated sodium hydrogen carbonate solution and water, the organic phase is dried with sodium sulphate, the solvent is evaporated off and the residue is crystallised with ether. 9.6 g (83%) of colourless crystals are obtained which can be recrystallised from isopropanol. Melting point: 242°–243° C.

$C_{22}H_{24}ClN_5O_2S$ (482.0) Calculated C=59.80, H 5.02, N 14.53 Found 59.63 4.95 14.73

The starting material is obtained as follows:

a) 50 g (0.29 mol) of ethyl 3-hydroxycyclohexanecarboxylate, $Bp_{18}$: 135°–140° C. (prepared by hydrogenation of 3-hydroxybenzoic acid ester) are mixed with 92.5 ml of chromosulphuric acid (133 g of chromium trioxide, 115 ml of concentrated sulphuric acid, diluted to 500 ml with water) in 600 ml of acetone and the mixture is stirred for 30 minutes at 35° C. The solution is decanted off from the dark green oil and the oil is extracted once more with acetone. The extracts are evaporated down in vacuo, the residue is taken up with methylene chloride, the solution is washed with water, dried and evaporated down. 50 g of ethyl 3-cyclohexanonecarboxylate are obtained in the form of a light yellow oil.

b) 50 g (0.29 mol) of the above-mentioned compound, 51 g (0.29 mol) of o-chlorocyanoacetophenone, 9.3 g of sulphur and 130 ml of dimethyl formamide are stirred and at 30°–35° C. the mixture is combined with 25.9 ml of triethylamine. It is stirred for a further 30 minutes, the dimethyl formamide is distilled off, the residue is taken up in ethyl acetate and washed with water. After drying it is evaporated down and chromatographed over $SiO_2$, using a mixture of methylene chloride and methanol (95:5) as eluant. From the eluate, 35–40 g of yellow crystals of 2-amino-5-ethoxycarbonyl-3-(2-chlorobenzoyl)- 4,5,6,7-tetrahydrobenzo[b]thiophene are obtained as the main fraction.
M.p. 136°–137° C.

c) 34 g (0.02 mol) of the amino ketone prepared as in Example b) yield 38 g of the N-bromoacetyl compound (m.p. 105°–107° C.) when reacted with 8.5 ml of bromoacetyl bromide in 300 ml of dioxan in the presence of 7.5 ml of pyridine; the N-bromoacetyl compound is then dissolved in 650 ml of anhydrous ethyl acetate. Ammonia is fed in with stirring for 2 hours at ambient temperature and the mixture is left to stand overnight. 100 ml of ice water are added, the organic phase is separated off, dried and concentrated by evaporation. 30–32 g of a reddish oil remain which are taken up in 600–700 ml of toluene for the diazepine cyclisation. 150 g of $SiO_2$ are added and the mixture is stirred for 2 hours at reflux temperature using a water separator. The solvent is decanted off and the residue is extracted several times with methanol with the application of heat. The methanol extracts are concentrated by evaporation and the residue is recrystallised from ethyl acetate. Yield: 23–25 g of 7-carbethoxy-5-(o-chlorophenyl)-6,7,8,9-tetrahydro- 1H,3H[1]benzothieno-[2,3-e]diazepin-2-one, m.p. 209°–211° C.

d) 36.2 g (0.97 mol) of the above diazepinone are taken up in 350 ml of diglyme, 15 g of sodium hydrogen carbonate and 30 g of phosphorous pentasulphide are added and the mixture is stirred for 4–5 hours at 75°–80° C. After cooling to ambient temperature 350 ml of water are gradually added whereupon the diazepine thione crystallises out. The crystals are suction filtered, washed with water, dissolved in methylene chloride and the solution is dried and evaporated down. The thione crystallises after the addition of ether. Yield: 30–32 g of yellow crystals, m.p. 197°–198° C.

e) 14 g (0.03 mol) of the above mentioned diazepine thione are dissolved in 170 ml of tetrahydrofuran and mixed with 2.7 g of hydrazine hydrate. The mixture is stirred for 30 minutes at ambient temperature, the solvent is distilled off and the residue is mixed with ether. Yield: 13 g of crystals, m.p. 199°–200° C.; they are taken up in 100 ml of ethanol and refluxed for 1 hour after the addition of 50 ml of triethylorthoacetate. The solvent is distilled off and the residue is chromatographed over $SiO_2$ (eluant: methylene chloride/methanol 98:2). The residue of the main fraction is recrystallised from ethyl acetate. Yield: 11.8 g (81% of theory) of colourless crystals of 4-(ethoxycarbonyl)-6-(2-chlorophenyl)-11-methyl- 2,3,4,5-tetrahydro-8H-[1] benzothieno[3,2-f][1,2,4]triazolo[4,3-a][1,4]diazepine, m.p. 183°–184° C.

f) 15 g (0.036 mol) of the ester described above are stirred with 150 ml of 2N ethanolic potassium hydroxide solution for 30 minutes at ambient temperature. The solution is then concentrated by evaporation in vacuo, the residue is taken up in water and adjusted to pH 5–6 with 2N hydrochloric acid after being cooled with ice. The carboxylic acid is extracted with methylene chloride. After working up, crystals of m.p. 312°–315° C. are obtained.

EXAMPLE 2

3-(Morpholin-4-yl-carbonyl)-6-(2-chlorophenyl)-11-methyl-2,3,4,5-tetrahydro-8H-[1]benzothieno[3,2-f][1,2,4]triazolo[4,3-a][1,4]diazepine 16 g (0.04 mol) of 3-Carboxy-6-(2-chlorophenyl)-11-methyl-2,3,4,5-tetrahydro-8H-[1]benzothieno[3,2-f][1,2,4]triazolo[4,3-a][1,4]diazepine and 5.3 g of N-hydroxybenzotriazole are suspended or dissolved in 150 ml of dimethyl formamide and 3.4 g (0.04 mol) of morpholine are added. Whilst stirring and cooling with ice, 9.7 g (0.04 g/mol) of dicyclohexylcarbodiimide are added and the mixture is stirred at 0°–5° C. for a further 20 to 24 hours. The dicyclohexylurea precipitated is suction filtered and the filtrate is evaporated down in vacuo. The residue is dissolved in 100 ml of 0.5N hydrochloric acid and the undissolved constituents are removed by suction filtering.

The filtrate is neutralised and extracted with methylene chloride. The residue of the methylene chloride phase is recrystallised from ethyl acetate/ether and yields 15–16 g of the title compound, m.p. 253°–255° C.

$C_{24}H_{24}ClN_5O_2$ (482.0) Calculated C=59.80 H 5.02 N 14.53 59.61 5.17 14.07

Starting from ethyl 4-hydroxy-cyclohexanecarboxylate ($Bp_{18}$: 142°–145° C.) the carboxylic acid used as starting compound is obtained by the method of preparation described in Example 1 via the following intermediate products:

| | |
|---|---|
| 2-Amino-3-(2-chlorobenzoyl)-6-ethoxycarbonyl-4,5,6,7-tetrahydrobenzo[b]-thiophene | Mp: 167–168° C. |
| Bromoacetyl derivative | Mp: 133–135° C. |
| Aminoacetyl derivative | Mp: 145–146° C. |
| Diazepin-2-one | Mp: 223–225° C. |
| 8-Carbethoxy-5-(2-chloro-phenyl)-6,7,8,9-tetrahydro-3H-[1]benzothieno[2,3-e]-diazepin-2-thione | Mp: 212–214° C. |

EXAMPLE 3

4-(Morpholin-4-yl-carbonyl)-11-cyclopropyl-6-(2-chlorophenyl)-2,3,4,5-tetrahydro-8H-[1]benzothieno[3,2-f][1,2,4]triazolo[4,3-a][1,4]diazepine Starting from 15 g (0.037 mol) of 4-carboxy-11-cyclopropyl-6-(2-chlorophenyl)-2,3,4,5-tetrahydro-8H-[1]benzothieno[3,2-f][1,2,4]triazolo[4,3-a][1,4]diazepine by reacting with 32 g of morpholine in dimethyl formamide using the method described in Example 2, 13.7 g of the title compound are obtained as a light yellow powder which begins to sinter at 175° C.

$C_{26}H_{26}ClN_5O_2S$ (508.1) Calculated C 61.47 H 5.53 N 13.78 Found 61.17 5.18 13.65

The starting material is prepared as follows:

9.14 g (0.022 mol) of 7-Carbethoxy-5-(2-chlorophenyl)-6,7,8,9-1H,3H-[1]benzothieno[2,3-e]diazepin-2-thione are dissolved or suspended in 100 ml of dioxan and after the addition of 2.14 g of cyclopropane carboxylic acid hydrazide the mixture is refluxed for 3 hours. After the solvent has been evaporated off the residue is chromatographed over a column filled with $SiO_2$ and eluted with methylene chloride/methanol (98:2). 8.6 g of a viscous reddish oil are obtained which is saponified with 85 ml of 2N ethanolic potassium hydroxide solution, without further purification, to obtain the acid.

EXAMPLE 3a 4-tert.Butylaminocarbonyl-6-(2-chlorophenyl)-11-methyl-2,3,4,5-tetrahydro-8H-[1]benzothieno[3,2-f][1,2,4]triazolo[4,3-a][1,4]diazepine 2.9 g (7 mmol) of the carboxylic acid from Example 1f) are combined with 1.3 ml (18 mmol) of thionyl chloride in 40 ml of anhydrous dichloromethane and the mixture is stirred for 30 minutes at ambient temperature. The suspension is evaporated down and after the addition of 25 ml (240 mmol) of tert.butylamine it is refluxed for 3 hours. It is then evaporated to dryness, taken up in dichloromethane, extracted with water. The residue of the organic phase is chromatographed on silica gel with dichloromethane/methanol (95:5) and then recrystallised from ethanol/ether. Yield: 1.2 g of the title compound, m.p.: 273° C.

Calculated: C 61.59 H 5.60 N 14.96 Cl 7.58 S 6.85 Found: C 61.49 H 5.83 N 14.74 Cl 7.49 S 6.74

EXAMPLE 4

3-(Morpholin-4-yl-carbonyl)-6-(2-chlorophenyl)-2,3,4,5-tetrahydro-8H-[1]benzothieno[3,2-f][1,2,4]triazolo[4,3-a][1,4]diazepine When 8-carbethoxy-5-(2-chlorophenyl)-6,7,8,9-tetrahydro-1H,3H-[1]benzothieno[2,3-e]diazepin-2-thione is reacted with hydrazine hydrate and then with triethylorthoformate the corresponding cyclised ester is obtained (wherein $R_1$ is hydrogen) and from this the carboxylic acid is obtained by saponification and the title compound is obtained therefrom, m.p.: 254°–256° C.

EXAMPLE 5

11-Bromo-3-(morpholin-4-yl-carbonyl)-6-(2-chlorophenyl)-2,3,4,5-tetrahydro-8H-[1]benzothieno[3,2-f][1,2,4]triazolo[4,3-a][1,4]diazepine 6.1 g (0.013 mol) of the morpholide, prepared according to Example 4, are dissolved or suspended in 50 ml of chloroform and 2.5 ml of pyridine are added. 0.9 ml of bromine dissolved in 10 ml of chloroform are added dropwise and the mixture is stirred overnight at ambient temperature. The reaction solution is washed with water, dried, concentrated by evaporation and chromatographed over $SiO_2$. The desired bromine compound, m.p. 253° C.) is obtained from the residue of the eluate.

EXAMPLE 6

11-Methoxy-3-(morpholin-4-yl-carbonyl)-6-(2-chlorophenyl)-2,3,4,5-tetrahydro-8H-[1]benzothieno[3,2-f][1,2,4]triazolo[4,3-a][1,4]diazepine 2.4 g of bromine compound prepared according to Example 5 are dissolved with 2.5 g of caustic potash (KOH) in 250 ml of methanol and refluxed for 1 hour. The methanol is distilled off, the residue is taken up in methylene chloride and the solution is washed with water. It is dried, concentrated by evaporation and the residue is triturated with ether.

Yield: 1.4–1.6 g, Mp. 207° C.

$C_{24}H_{24}ClN_5O_3S$ (498.0) Calculated: C 57.88, H.4.86, N 14.06 Found C 57.92 4.81 14.01

EXAMPLE 7

3-(Morpholin-4-yl-carbonyl)-5-(2-chlorophenyl)-10-methyl-3,4-dihydro-2H,7 H-cyclopenta[4,5]thieno[3,2-f][1,2,4]triazolo[4,3-a][1,4]diazepine 15 g (0.038 mol) of 3-carboxy-5-(2-chlorophenyl)-10-methyl-3,4-dihydro-2H,7 H-cyclopenta[4,5]thieno[3,2-f][1,2,4]triazolo[4,3-a][1,4]diazepine are converted into the amide with 3.5 g of morpholine using dicyclohexylcarbodiimide as described in Example 2. 15–16 g of a powder are obtained, m.p. 150° C. When recrystallised from ethanol the compound melts at 167°–168° C. The compound contains 1–2% of alcohol of crystallisation. $^1$H-NMR (CDCl$_3$): δ7.22–7.59 (m, 4H, aryl-H); 4.94 (s, broad, 2H, CH$_2$-7 ring); 2.06–4.00 (m, 13H, cyclopentenyl-H, morpholine-H); 2.67 (s, 3H, CH$_3$-triazole ring).

The acid used is prepared as follows:

a) 41.6 g (0.27 mol) of ethyl cyclopentanon-3-carboxylate (H. Stetzer and R. Kuhlmann, Liebigs Ann. Chem. 1979, 944; Bp. 70°–74° C.), 47.8 g of o-chlorocyanoacetophenone and 9 g of sulphur are suspended or dissolved in 120 ml of dimethyl formamide and mixed with 26.5 ml of triethylamine in 120 ml of ethanol, the mixture is heated for 30–45 minutes to 30°–60° C. and then worked up as in Example 1b. After chromatography, 29–30 g of 2-amino-3-(2-chlorobenzoyl)-5-ethoxycarbonyl-5,6-dihydro-4H-cyclopenta[b]thiophene are obtained in the form of yellow crystals, m.p.: 121°–122° C.

b) Bromoacetylation, reaction with ammonia and cyclisation in toluene in the presence of SiO$_2$ as in Example 1c yield 7-carbethoxy-5-(2-chlorophenyl)7,8-dihydro-3H,6H-cyclopenta[4,5]thieno[2,3-e]diazepin2-one in the form of colourless crystals, m.p. 158°–160° C.

The diazepinone is further reacted as in Example 1d. The ester of the triazolo compound is obtained, m.p. 175°–176° C. and from this the corresponding carboxylic acid is obtained by saponification.

Separation of isomers

The above racemate (Example 7, m.p. 167°–168° C.) is separated into its enantiomers on a chiral L-polyamide silica gel (HPLC) column (eluant: dioxan/n-hexane 7:3).

The (−)-enantiomer (alpha)=−26,5 (C=8,85, dioxane) is obtained as well as the corresponding (+)-enantiomer (alpha)=+26,4 (C=11,4, dioxane).

EXAMPLE 7a

3-(n-Hexadecylamino-carbonyl)-5-(2-chlorophenyl)-10-methyl-3,4-dihydro-2H,7 H-cyclopenta[4,5]thieno[3,2-f][1,2,4]triazolo[4,3-a][1,4]diazepine 6 g (15 mmol) of the corresponding carboxylic acid (see Example 7) are reacted with 4.5 g (18 mmol) of hexadecylamine, 4.4 g of dicyclohexylcarbodiimide and 2.4 g of hydroxybenzotriazole using the method described in Example 2.

7 g of a light yellow oil are obtained (75% of theory)

$^1$H-NMR (CDCl$_3$) δ7.26–7.53 (4H, m, aryl-H); 5.86 ($^1$H, t, J=7 Hz, NH); 4.86 (2H, s, broad, CH$_2$-7-ring); 2.71 (3H, s, CH$_3$ C=N); 1.39–3.43 (7H, m, cyclopentenyl-H, NCH$_2$); 1.26. (28H, s, hexadecanyl); 0.88 (3H, t, J=6 Hz, 3H, CH$_3$-hexadecanyl).

EXAMPLE 7b

3-(Dioctylamino-carbonyl)-5-(2-chlorophenyl)-10-methyl-3,4-dihydro-2H,7 H-cyclopenta[4,5]thieno[3,2-f][1,2,4]triazolo[4,3-a][1,4]diazepine 2 g (5 mmol) of the above carboxylic acid (Example 7) when reacted with 1.5 g (6 mmol) of dioctylamine using the above method yield the title compound.

2 g (65% of theory) of viscous oil, $^1$H-NMR (CDCl$_3$): δ7.33–7.55 (m, 4H, aryl-H); 4.92 (s, broad, 2H, CH$_2$-7-ring); 2.74 (s, 3H, CH$_3$C=N); 1.04–3.81 (m, 33H, cyclopentyl H, octylaminoCH$_2$); 0.89 (t, J=6 Hz, CH$_3$ octylamine).

EXAMPLE 7c

3-(Dipropylaminocarbonyl)-5-(2-chlorophenyl)-10-methyl-3,4-dihydro-2H,7 H-cyclopenta[4,5]thieno[3,2-f][1,2,4]triazolo[4,3-a][1,4]diazepine 4.8 g (10 mmol) of the diallylamide (Example 138) are dissolved in 250 ml of methanol and after the addition of 1 g of 5% palladium/charcoal the solution is hydrogenated under a slight overpressure. The uptake of hydrogen is quantitative. After filtration and removal of the solvent the title compound is left as a white foam.

$^1$H NMR (CDCl$_3$): δ7.22–7.58 (m, 4H, aryl-H); 4.94 (s, broad, 2H, CH$_2$ 7-ring; 2.69 (s, 3H, CH$_3$—C=N); 1.23–3.41 (m, 13H, cyclopentenyl-H, N—CH$_2$CH$_2$—CH$_3$; 0.82 (t, J=7 Hz, 6H, N—CH$_2$—CH$_2$—CH$_3$).

EXAMPLE 8

4-(Morpholin-4-yl-carbonyl)-5-(2-chlorophenyl)-10-methyl-7H-cyclopenta[4,5]thieno[3,2-f][1,2,4]triazolo[4,3-a][1,4]diazepine 20 g (0.05 mol) of 4-carboxy-5-(2-chlorophenyl)-10-methyl- 3,4-dihydro-2H,7H-cyclopenta[4,5]thieno[3,2-f][1,2,4]triazolo[4,3-a][1,4]diazepine, m.p. 285°–286° C., are reacted with 4.6 g of morpholine by the dicyclohexylcarbodiimide method to yield the corresponding amide. After working up, 13 g (55% of theory) of the crystalline title compound are obtained, m.p. 298°–300° C. (methylene chloride/ether)

$C_{23}H_{22}ClN_5O_2$ (467.9) Calculated C 59.03, H 4.74 N 14.97 58.84 4.73 14.69

The carboxylic acid used as starting compound is synthesised analogously to Example 7 from commercial ethyl cyclopentanon-2-carboxylate.

2-Amino-4-carbethoxy-3-(2-chlorobenzoyl)- M.p.: 122°–124° C. 5,6-dihydro-4H-cyclopenta[b]thiophene

| Bromoacetyl compound | 148–150° C. |
| Aminoacetyl compound | 198–200° C. |
| Diazepinone | 178–179° C. |
| Ethyl ester of triazolodiazepine | 285–286° C. |

EXAMPLE 9

5-(Morpholin-4-yl-carbonyl)-7-(2-chlorophenyl)-12-methyl-3,4,5,6-tetrahydro-2H,9H-cyclohepta[4,5]thieno[3,2-f][1,2,4]triazolo[4,3-a][1,4]diazepine 0.75 g of the corresponding carboxylic acid, when reacted with 0.18 g of morpholine by the dicyclohexylcarbodiimide method described in Example 2, yield the desired amide, m.p. 290°–291° C., $C_{25}H_{26}ClN_5O_2$ (496.0) Calculated: C=60.53 H 5.28 N 14.12 60.12, 5.36 14.93

The carboxylic acid may be prepared, starting from 3-ethoxycarbonyl cycloheptanone (A. Mondau and G. Humman, Chem. Ber. 105, 1459 (1972)) by a multi-step synthesis analogously to the method described hereinbefore.

M.p.: of the 5-carboethoxy-cyclohepta-thieno-triazolodiazepines 187°–188° C.

EXAMPLE 10

4-(Morpholin-4-yl-carbonyl)-6-(2-chlorophenyl)-11-methyl-2,3,4,5-tetrahydro-8H-[1]benzothieno[3,2-f]imidazo[1,2-a][1,4]diazepine 5 g (0.012 mol) of the corresponding carboxylic acid are reacted with 1.2 g of morpholine by the dicyclohexylcarbodiimide method as described above and after working up yield 4.0 g of the morpholide, m.p.: 248°–250° C.

$C_{25}H_{25}ClN_4O_2S$ (481.0) C 62.42, H 5.24, N 11.65 62.31 5.36 10.99

The acid is obtained by the following method:

25 g (0.06 mol) of the diazepine thione (prepared according to Example 1d), m.p. 197°–198° C.) are mixed with 10 g of propargylamine in 300 ml of dioxan at ambient temperature and the mixture is refluxed for 2 to 3 hours. It is evaporated down, the residue is taken up in methylene chloride and extracted with water; the organic phase is dried and after evaporation and trituration with ether 18.7 g of crystals are obtained, m.p.: 179°–181° C.

8 g (0.018 mol) of the aminoalkyne prepared above are stirred with 35 ml of conc. sulphuric acid for 15 minutes at 100° C. The mixture is poured onto ice, adjusted to pH 5 using NaOH and the carboxylic acid formed is extracted with methylene chloride/methanol (95:5). 5–6 g of carboxylic acid are obtained, m.p.: 275°–278° C., from the organic phase after working up in the usual way.

EXAMPLE 10a

3-Carboxy-5-(2-chlorophenyl)-10-methyl-3,4-dihydro-2H,7H-cyclopenta[4,5]thieno[3,2-f]imidazo[1,2-a][1,4]diazepine 0.4 g (0.84 mmol) of 7-carbomethoxy-5-(2-chlorophenyl)2-(2-methyl-1,3-dioxolan- 2-yl-methylamino)-7,8-dihydro-3H,6H-cyclopenta[4,5]thieno[3,2-f][1,4]diazepine are heated in 4 ml of concentrated sulphuric acid for 5 minutes at 50° C. After dilution with water the reaction mixture is neutralised with concentrated sodium hydroxide solution, whilst cooling with ice, the solution is extracted with methylene chloride and the organic phase is washed, dried and evaporated down. The residue obtained consists of 0.22 g (65% yield) of acid.

$^1$H-NMR (CD$_3$OD): δ7.40–7.61 (m, 4H, aryl-H); 6.93 (qu, J<1 Hz, 1H, CH=); 4.22 (s, broad, 2H, CH$_2$-7-ring); 3.18–3.67 (m, 5H, CH$_2$, CH, 5-ring); 2.48 (d, J<1 Hz, 3H, CH$_3$).

Synthesis of the precursors, some of which are known:

N-acetonylphthalimide, m.p. 103°–105°, is obtained from chloroacetone and potassium phthalimide in a 93% yield and is then ketalised with ethylene glycol and concentrated sulphuric acid in toluene using a water separator in a 69% yield to obtain the N-acetonylphthalimide ethylene ketal, m.p. 91°–93° C. The phthalimide cleaving must be carried out with hydrazine hydrate in a molar ratio in ethanol, whereupon the resulting 2-aminomethyl-2-methyl-dioxolan is obtained in ethanolic solution and, after removal of the solvent, without further purification it is reacted with 7-carbomethoxy-5-(2-chlorophenyl)- 7,8-dihydro-3H,6H-cyclopenta[4,5]thieno[2,3-e][1,4]diazepin-2-thione, prepared analogously to Example 7b and 1d, in dioxan in a 45% yield to obtain 7-carbomethoxy-5-(2-chlorophenyl)-2-(2-methyl-1,3-dioxolan- 2-yl-methylamino)-7,8-dihydro-3H,6H-cyclopenta[4,5]thieno[3,2-f][1,4]diazepine, m.p. 166°–168° C.

EXAMPLE 10b

3-(n-Hexadecylamino-carbonyl)-5-(2-chlorophenyl)-10-methyl-3,4-dihydro-2H,7H-cyclopenta[4,5]thieno[3,2-f]imidazo[1,2-a][1,4]diazepine 1.9 g (4.8 mmol) of the corresponding carboxylic acid (m.p. 175° C.) (obtained from the diazepin-2-one of Example 7 analogously to the method described in Example 10 or as given in Example 10a), when reacted with 1.5 g (6 mmol) of n-hexadecylamine, yield 2 g (69% of theory) of the title compound in the form of a viscous oil. $^1$H-NMR (CDCl$_3$): δ7.25–7.49 (m, 4H, aryl-H); 6.89 (qu, J<1 Hz, 1H, CH=); 5.69 (t, J=6 Hz, 1H, NH); 4.17 (s, broad, 2H, CH$_2$-7 ring). 3.05–3.37 (m, 7H, CH$_2$, CH, 5-ring; NCH$_2$); 2.44 (d, J<1 Hz, 3H, CH$_3$—C=); 0.99–1.53 (m, 28H, N—CH$_2$—(CH$_2$)$_{14}$); 0.88 (t, J=8 Hz, 3H, CH$_3$—(CH$_2$)$_n$).

EXAMPLE 11

4-(Diethylaminocarbonyl)-6-(2-chlorophenyl)-11-methyl-2,3,4,5-tetrahydro-8H-[1]benzothieno][3,2-f]imidazo[1,2-a][1,4]diazepine The amide, m.p. 201°–203° C. is obtained from the corresponding acid (Example 10) analogously by reacting with diethylamine.

$C_{25}H_{27}ClN_4OS$ (467.2) C 64.29 H 5.83 N 12.00 64.08 5.90 11.87

EXAMPLE 12

4-(Diethylaminocarbonyl)-6-(2-chlorophenyl)-10-methyl-2,3,4,5-tetrahydro-8H-[1]benzothieno[3,2-f]imidazo[1,2-a][1,4]diazepine 4.2 g (0.009 mol) of diazepine thione (see Example 1d) are refluxed for 3 hours with 3 g of 2-aminopropionaldehyde diethylacetal and 0.75 g of p-toluenesulphonic acid in 80 ml of dioxan. The reaction mixture is evaporated down, taken up in methylene chloride, washed with water, dried, evaporated down once more and then isopropylether is added, whereupon the intermediate compound crystallises. Yield 2.7 g.

When heated for 15 minutes in concentrated sulphuric acid (100° C.) and worked up, this derivative yields the carboxylic acid. The amide is prepared from this as described before.

EXAMPLE 12a 3-(Morpholin-4-yl-carbonyl)-5-(2-chlorophenyl)-9-methyl-10-bromo-3,4-dihydro-2H,7H-cyclopenta[4,5]thieno[3,2-f]imidazo[1,2-a][1,4]diazepine 1 g (2.1 mmol) of 3-(morpholin-4-yl-carbonyl)-5-(2-chlorophenyl)-9-methyl- 3,4-dihydro-2H,7H-cyclopenta[4,5]thieno[3,2-f]imidazo[1,2-a][1,4]diazepine are placed in 30 ml of anhydrous trichloromethane at 0.22 g of pyridine and 0.4 g (2.5 mmol) of bromine are added dropwise at ambient temperature. After 16 hours the mixture is washed twice with water, the organic phase is dried with $Na_2SO_4$ and concentrated by evaporation and the residue is filtered over a column filled with silica gel ($CH_2Cl_2$ containing about 4% $CH_3OH$). 0.5 g of title compound sintering from 135° C. are obtained from the concentrated eluate by trituration with ether.

EXAMPLE 12b

3-Carboxy-5-(2-chlorophenyl)-9-methyl-3,4-dihydro-2H,7H-cyclopenta[4,5]thieno[3,2-f]imidazo[1,2-a][1,4]diazepine 7.3 g (14.5 mmol) of 2-(1,1-diethoxy-prop-2-yl-amino)-5-( 2-chlorophenyl)-7-methoxycarbonyl-7,8-dihydro-3H,6H-cyclopenta[4,5]thieno[2,3-e]diazepine are suspended in 35 ml of conc. sulphuric acid and stirred for 15 minutes at 100° C. The reaction mixture is then poured onto ice and made alkaline with ammonium hydroxide (pH 9) and then adjusted to pH 6 using 2N HCl. It is extracted with dichloromethane (3×150 ml), the dried organic phase is filtered over kieselguhr/charcoal, then concentrated by evaporation and the residue is triturated with a little ether. 4.3 g of the title compound are obtained, m.p. 160°–162° C.

Preparation of the starting compound:

10 g (25.6 mmol) of the corresponding diazepin-2-thione and 9.5 g (65 mmol) of 2-amino-propionaldehyde diethylacetal are refluxed in 100 ml of dioxan. After reacting for 2 hours, the solvent is distilled off and the residue is combined with dichloromethane/water. The organic phase is separated off and dried and then filtered over silica gel/charcoal, concentrated by evaporation and the residue is filtered over a column filled with silica gel (dichloromethane containing about 2% $CH_3OH$). The concentrated eluate is triturated with diisopropylether. 7.4 g of 2-(1,1-diethoxy-prop-2-yl-amino)-5-(2-chlorophenyl)-7-methoxycarbonyl-7,8-dihydro-3H,6H-cyclopenta[4,5]thieno[2,3-e]diazepine are obtained in the form of greyish-brown crystals, m.p. 137°–140° C.

EXAMPLE 12c

3-Carboxy-5-(2-chlorophenyl)-3,4-dihydro-2H,7H-cyclopenta[4,5]thieno[3,2-f]imidazo[1,2-a][1,4]diazepine Starting from 9.8 g (0.02 mol) of 2-(1,1-diethoxyethylamino)-5-(2-chlorophenyl)- 7-methoxycarbonyl-7,8-dihydro-3H,6H-cyclopenta[4,5]thieno[2,3-e]diazepine, 7.5 g of the title compound are obtained analogously to the preceding Example in the form of grey crystals, m.p. 315° C.

Preparation of the starting compound:

Analogously to Example 12, 9.8 g of the desired acetal are obtained in the form of brown crystals, m.p. 125° to 125° C., from 10 g (25.6 mmol) of the corresponding diazepine thione and 8.7 g (65 mmol) of aminoacetaldehyde diethylacetal.

EXAMPLE 13

6-(2-Chlorophenyl)-11-methyl-4,5-dihydro-3H,8H-[1]benzothieno[3,2-f][1,2,4]triazolo[4,3-a][1,4]diazepin-2-one

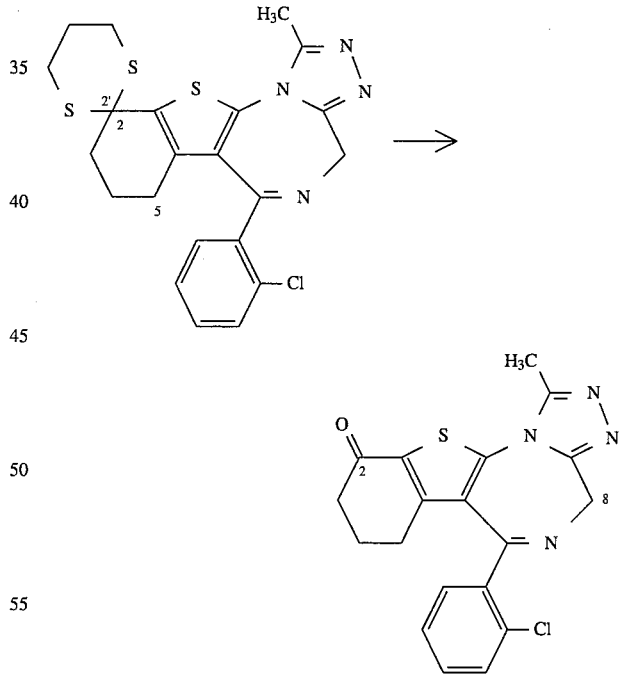

A suspension of 8.5 g (0.018 mol) of spiro[6-(2-chlorophenyl)-11-methyl- 2,3,4,5-tetrahydro-8H-[1]benzothieno[3,2-f][1,2,4]triazolo[4,3-a][1,4]diazepine-2,2'(1,3)dithiane], 9.77 g (0.036 mol) of mercury(II) chloride and 3.98 g (0. 018 mol) of mercury (II) oxide in 270 ml of 90% aqueous methanol is refluxed for 2 hours with stirring. The reaction mixture is then filtered off and the residue is washed several times with chloroform. The filtrates are combined and concentrated by evaporation in vacuo. The residue is dissolved in chloroform and the resulting solution is extracted several times with dilute aqueous ammonium chloride solution. After drying over anhydrous sodium sulphate the organic phase concentrated by evaporation. The residue is purified by chromatographic treatment on silica gel using acetone as eluant. 4.5 g (65.4% of theory) of crystalline ketone are obtained, m.p. 212°–218° C., which can be recrystallised from acetonitrile.

M.p.: 219°–222° C.

$C_{19}H_{15}ClN_4OS$ (382.88) Calculated: C 59.60 H 3.95 N 14.63 Cl 9.26 S 8.37 Found: 59.47 3.97 14.66 9.20 8.23

Preparation of the starting material a) 2-Acetylamino-3-(2-chlorobenzoyl)-5,6-dihydro-4H-benzo[b]thiophen-7-one

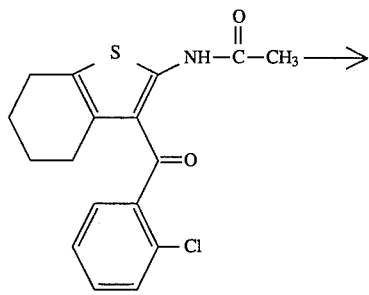

A solution of 20 g (0.02 mol) of chromium(VI) oxide in 60 ml of water is added dropwise, with stirring, within about 30 minutes at 20°–30° (cooling with ice) to a suspension of 13.35 g (0.04 mol) of 2-acetylamino-3-(2-chlorobenzoyl)-5,6-dihydro-7H-benzo[b]thiophene (m.p. 173°–176° C.) [prepared by reacting (2-amino-3-(2-chlorobenzoyl)-4,5,6, 7-tetrahydro-benzo[b]-thiophene[1]) with acetic acid anhydride]. The reaction mixture is stirred for a further 2 hours, diluted with 500 ml of water and then extracted several times with ethyl acetate the combined ethyl acetate phases are washed successively with dilute aqueous ammonia solution and water, dried over sodium sulphate and concentrated by evaporation. The residue is suspended with ether and suction filtered. 3.8 g (27.3% of theory) of crystals are obtained, m.p. 198°–202° C., which can be recrystallised from methanol. M.p. 203°–206° C.

[1]) F. J. Tinney et. al., K. Med. Chem. 17/6, 624 ff (1974)

$C_{17}H_{14}ClNO_3S$ (347.83) Calculated: C 58.70 H 4.06. N 4.03 S 9.22 Found: 58.71 4.13 4.12 9.13 b) 2-Amino-3-(2-chlorobenzoyl)-5,6-dihydro-4H-benzo[b]thiophen-7-one 26.5 g (0.076 mol) of 2-acetylamino-3-(2-chlorobenzoyl)-5,6-dihydro- 4H-benzo[b]thiophen-7-one are added with stirring to a solution of 5.6 g (0.1 mol) of potassium hydroxide in 150 ml of methanol. A solution is formed from which the aminoketone is precipitated after a short time. After 2 hours the crystals are suction filtered, washed with methanol and dried.

Yield: 18.6 (79.8% of theory); m.p.: 224°–226° C.

c) Spiro[2-amino-3-(2-chlorobenzoyl)-4,5,6,7-tetrahydrobenzo[b]thiophen-7,2'(1,3)dithiane]

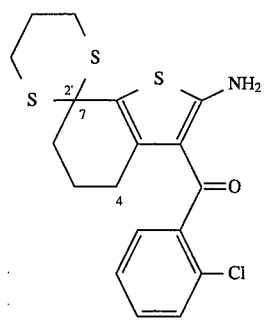

Hydrogen chloride is introduced for 7 hours, whilst cooling with ice, into a suspension of 18.5 g (0.06 mol) of the amino ketone obtained in b) and 6.55 g (0.06 mol) of 1,3-propandithiol in 200 ml of chloroform. The reaction mixture is stirred overnight at ambient temperature. After the addition of methanol a clear solution is obtained which is concentrated to dryness in vacuo. The residue is suspended with acetonitrile. The crystals obtained are purified by column chromatography over silica gel using chloroform as eluant.

Yield: 12.6 g (52.6% of theory); m.p.: 211°–212° C. (acetonitrile).

d) Spiro[2-bromoacetylamino-3-(2-chlorobenzoyl)-4,5,6, 7-tetrahydro-benzo[b]thiophen- 7,2'(1,3)dithian] is obtained analogously to Example 14b).

M.p.: 162°–164° C. (decomposition).

e) Spiro[5-(2-chlorophenyl)-6,7,8,9-tetrahydro-1H,3H-[1H]benzothieno[2,3-e]-[1,4]diazepin-2-on-9,2'(1, 3)dithian]

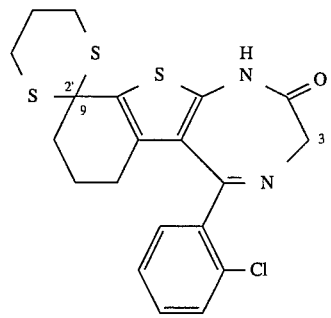

43.8 g (0.085 mol) of the N-bromoacetyl compound prepared in d are reacted analogously to Example 14. 34.8 g (95.4% of theory) of the diazepinone are obtained [m.p. 263°–265° C. (decomposition)].

f) Spiro[6-(2-chlorophenyl)-11-methyl-2,3,4,5-tetrahydro-8H-[1]benzothieno[3,2-f][1,2,4]triazolo[4,3-a][1,4]diazepin-2,2'(1,3)-dithian]

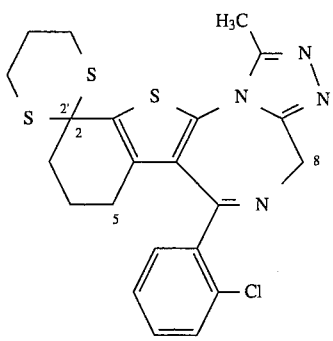

M.p. 267°–270° C. The compound is obtained starting from the diazepinone described in e) analogously to Example 14d and 14e.

EXAMPLE 14

6-(2-Chlorophenyl)-11-methyl-4,5-dihydro-2H, 8H-[1]-benzothieno[3,2-f][1,2,4]triazolo[4,3-a][1,4]diazepin-3-one

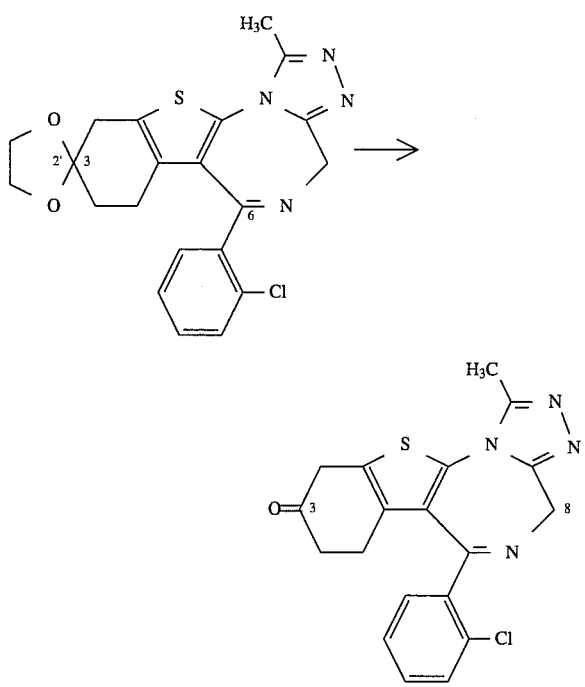

8.5 g (0.02 Mol) of spiro[6-(2-Chlorophenyl)-11-methyl-2,3,4,5-tetrahydro-8H-[1]benzothieno[3,2-f][1,2,4]triazolo[4,3-a][1,4]diazepin-3,2'(1,3)dioxalan] are added to 85 ml of 4N hydrochloric acid and the reaction mixture is stirred at ambient temperature for 30 minutes. The reaction solution is then extracted with chloroform. The aqueous phase is made alkaline with concentrated ammonia solution and extracted with chloroform. The chloroform solution is washed with water, dried over sodium sulphate and concentrated by evaporation in vacuo. The residue is chromatographed on a silica gel column in order to purify it (eluant: chloroform/methanol 95:5). 4.4 g (57.7% of theory) of the ketone are obtained, m.p. 200°–204° C.

The title compound, which is analytically pure, has a melting point of 202° C.–204° C. (DMF/ether).

$C_{19}H_{15}ClN_4OS$ (382.82) Calculated: C 59.60 H 3.95 N 14.63 Cl 9.26 S 8.37 Found: 59.34 3.71 14.46 9.11 8.05

The starting material may be obtained as follows:

a) Spiro[2-amino-3-(2-chlorobenzoyl)-4,5,6,7-tetrahydrobenzo[b]thiophen-6,2'(1,3)dioxolan]

A solution of 81.7 g (0.52 mol) of 1,4-dioxaspiro[4,5]decan-8-one and 93.5 g (0.52 mol) of o-chloro-2-cyanoacetophenone in 240 ml of dimethyl formamide is mixed successively with 16.7 g of sulphur and 48 ml of triethylamine with stirring. A slightly exothermic reaction takes place, with a clear solution gradually being formed. It is stirred for a further 30 minutes, 270 ml of alcohol are added and the reaction solution is heated to 60° C. for 4 hours. The solvents are then distilled off in vacuo. The crude product thus obtained is stirred with ethyl acetate and dilute common salt solution. The crystals obtained are suction filtered, washed with ether and dried.

Yield 108 g (59% of theory); m.p. 176°–178° C.

The analytically pure aminoketone has a melting point of 179°–182° C. (ethyl acetate).

$C_{17}H_{16}ClNO_3S$ (349.85) Calc.: C 58.36 H 4.61 N 4.00 Cl 10.14 S 9.17 found: 58.27 4.58 3.92 10.03 9.15 b) Spiro[2-(bromoacetylamino)-3-(2-chlorobenzoyl)-4,5,6,7-tetrahydro-benzo[b]thiophen- 6,2'(1,3)dioxolan]

171 g (0.49 mol) of the aminoketone obtained in a) are reacted with 110.4 g of bromoacetylbromide in dioxan with the addition of 44 g of pyridine. 215.8 g (94% of theory) of the bromoacetyl compound are obtained, m.p. 155°–157° C.

c) Spiro[5-(2-chlorophenyl)-6,7,8,9-tetrahydro-1H,3H-[1]benzothieno[2,3-e][1,4]diazepin-2-on-8,2'(1,3)dioxalan]

At ambient temperature, 70 g (0.15 mol) of the N-bromoacetyl compound obtained in b) are added to 1200 ml of ethyl acetate saturated with ammonia gas. After it has all been added ammonia gas is introduced for a further 2 hours and the mixture is left to react for a further 12 hours with stirring. The inorganic precipitate is removed by suction filtering and the filtrate is concentrated by evaporation in vacuo. For cyclisation the crude amino acetyl compound is taken up in 800 ml of toluene, 240 g of silica gel are added and the mixture is refluxed for 4 hours with stirring using a water separator. After cooling the silica gel is filtered off and the diazepine obtained is extracted with hot methanol. The residue obtained after concentration of the combined extracts is suspended in ethyl acetate, suction filtered and washed thoroughly with ether.

45.8 g (79.2% of theory) of the diazepinone are obtained [M.p. 262°–263° C. (decomposition)].

d) Spiro[5-(2-chlorophenyl)-6,7,8,9-tetrahydro-1H,3H-[1]benzothieno[2,3-e][1,4]diazepin-2-thion-8,2'-(1,3)dioxolan]

A suspension of 40.5 g (0.1 mol) of the diazepin-2-one obtained in c) and 40.45 g (0.1 mol) of Lawesson Reagent (Aldrich)® in 750 ml of tetrahydrofuran is refluxed for 2 hours. The solvent is distilled off and the remaining dark oil is purified by column chromatography over neutral aluminium oxide/activity stage III, using first chloroform and then a mixture of chloroform and methanol (95: 5) as eluant. The diazepin-2-thione obtained in crystalline form on concentration of the main fractions is suspended with ether and suction filtered.

Yield: 28.5 g (68.4% of theory); m.p. 203°–210° (decomposition). The pure title compound melts at 213°–214° C. (decomposition) (from toluene).

e) Spiro[6-(2-chlorophenyl)-11-methyl-2,3,4,5-tetrahydro-8H-[1]benzothieno[3,2-f][1,2,4]triazolo[4,3-a][1,4]diazepin-3,2'(1,3)-dioxolan]

A solution Of 11.8 g (0.029 mol) of the diazepin-2-thione obtained in d) in 120 ml of tetrahydrofuran is combined with 5.45 g (0.11 mol) of hydrazine hydrate and stirred for 1 hour at ambient temperature.

The solvent is distilled off in vacuo. The brown syrup remaining is taken up in chloroform, the solution is washed several times with water, then dried and evaporated down.

The residue (10.2 g of crude hydrazino compound) is suspended in 100 ml of ethanol and refluxed for 45 minutes after the addition of 18 ml of triethylorthoacetate. The reaction solution is concentrated by evaporation in vacuo. The crystalline residue is suspended in a little ethyl acetate and suction filtered.

Yield: 7.6 g (61% of theory); m.p. 218°–220° C. The analytically pure title compound has a melting point of 224°–225° C. after recrystallisation from ethyl acetate.

$C_{21}H_{19}ClN_4O_2S$ (426.94) Calc.: C 59.08 H 4.49 N 13.12 Cl 8.31 S 7.51 Found: 59.26 4.45 12.96 8.23 7.44

EXAMPLE 15

Spiro[2-amino-3-(2-chlorobenzoyl)-4,5,6,7-tetrahydro-benzo[b]thiophen- 5,2'(1,3)dioxolan]

Starting from 20.7 g (0.133 mol) of 1,4-dioxaspiro[4,5] decan-7-one [M. W. Cronyn et al., J.A.C.S. 74, 3331–3333 (1952)], 23.69 g (0.133 mol) of o-chloro-2-cyanoacetophenone, 4.29 g of sulphur and 12.2 ml of triethylamine, 34.2 g of crude product are obtained analogously to Example (14a) from which 2.8 g of the title compound are isolated by column chromatography (SiO$_2$/chloroform).

M.p.: 216°–218° C. (toluene). $C_{17}H_{16}ClNO_3S$ (349.85) Calculated: C 58.36 H 4.61 N 4.00 Cl 10.14 S 9.17 Found: 58.66 4.60 3.86 9.96 9.20

EXAMPLE 16

2-Hydroxy-6-(2-chlorophenyl)-11-methyl-2,3,4,5-tetrahydro-8H-[1]benzothieno[3,2-f][1,2,4]triazolo[4,3-a][1,4]diazepine

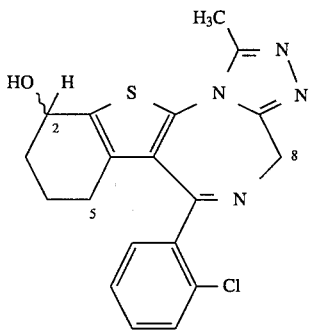

A suspension of 0.38 g (0.001 mol) of 6-(2-chlorophenyl)-11-methyl-4,5-dihydro- 3H,8H-[1]benzothieno[3,2-f][1,2,4]triazolo[4,3-a][1,4]diazepin-2-one in 3.8 ml of methanol is combined with 0.038 g (0.00 mol) of sodium borohydride with stirring. The reaction solution is then stirred for a further hour at ambient temperature mixed with a little water and concentrated by evaporation in vacuo. The residue is taken up in chloroform/water and the chloroform solution is extracted several times with water. The organic phase is dried over anhydrous sodium sulphate and the solvent is distilled off. The cloudy resin remaining is dissolved in acetone and filtered over a small column of silica gel. The residue obtained on evaporation of the eluate is crystallised with ethyl acetate.

Yield: 170 mg (44.3% of theory); m.p. 217°–219° C.

$C_{19}H_{17}ClN_4OS$ (384.9) Calculated: C 59.29 H 4.45 N 14.56 Found: 59.03 4.42 14.39

EXAMPLE 17

4-(Hydroxymethyl)-6-(2-chlorophenyl)-11-methyl-2,3,4,5-tetrahydro-8H-[1]benzothieno[3,2-f][1,2]triazolo[4,3-a][1,4]diazepine 10 g (0.0227 Mol) of the ethyl ester from Example 1e are placed in 100 ml of anhydrous THF, 0.52 g (0.0136 Mol) of lithium aluminium hydride is added in batches and the mixture is refluxed for 1 hour. The reaction mixture is decomposed with 0.5 ml of water, 0.5 ml of 15% sodium hydrixode solution and 1.5 ml of water, the precipitate is suction filtered, the filtrate is evaporated down, the residue is taken up in methylene chloride, the solution is washed with water and dried and the solvent is removed. The reaction mixture is chromatographed on silica gel with methylene chloride/methanol 9:1 as eluant and crystallized by trituration with ethyl acetate or acetone. 6.6 g (yield 93%) of the desired compound are obtained, m.p. 168°–172° C.

EXAMPLE 18

3-(Hydroxymethyl)-5-(2-chlorophenyl)-3,4-dihydro-2H,7H-cyclopenta[4,5]thieno[3, 2-f][1,2,4]triazolo[4,3-a][1,4]diazepine Analogously to Example 1, methyl cyclopentan-3-on-carboxylate, pb$_9$=95°–98° C., in a 61% yield is reacted to obtain 2-amino-3-(2-chlorobenzoyl)-5-carbomethoxy-5,6-dihydro-4H-cyclopenta[b]thiophen, m.p. 120°–125° C.

Bromoacetylation and subsequent reaction with ammonia yield oils, in quantative yield.

Cyclisation to produce 7-carbomethoxy-5-(2-chlorophenyl)-6,7-dihydro-1H,3H,8 H-cyclopenta[4,5]thieno[2,3-e][1,4]diazepin-2-one, m.p. 200°–205° C., results in a 78% yield.

The 3-carbomethoxy-5-(2-chlorophenyl)3,4-dihydro-2H, 7H-cyclopenta[4,5]thieno[3,2-f][1,2,4]triazolo[4,3-a][1,4] diazepine, m.p. 178°–181° C., which is obtainable therefrom in a 51% yield in the usually way is reduced as follows.

4.5 g (0.011 Mol) of the methyl ester and 1 g (0.0275 Mol) of sodium borohydride are refluxed in 40 ml of tert.-butanol and 10 ml of anhydrous methanol are added dropwise. After 60 minutes the solution is concentrated by evaporation, the residue is distributed in methylene chloride/water, the organic phase is dried, and after removal of the solvent, the residue is chromatographed on silica gel using methylene chloride/methanol 98:2 to 96:4 as eluant. By triturating with ether, 2.6 g of crystals, m.p. 182°–184° C., are obtained in a 76% yield.

EXAMPLE 19

3-Acetoxymethyl-5-(2-chlorophenyl)-10-methyl-3,4-dihydro-2H,7H-cyclopenta[4,5]thieno[3,2-f][1,2,4]triazolo[4,3-a][1,4]diazepine 0.21 ml (0.003 Mol) of acetylchloride are added dropwise at ambient temperature to 1.2 g (0.003 Mol) of the compound of Example 18 and 0.42 ml (0.003 Mol) of triethylamine in 20 ml of anhydrous methylene chloride, the mixture is stirred for 24 hours, extracted with water and, after drying, the solvent is eliminated. The residue is chromatographed on silica gel using acetone/methanol 9:1 as eluant and 0.55 g of a yellow oil are obtained (yield 42%).

EXAMPLE 20

4-Methanesulfonyloxymethyl-6-(2-chlorophenyl)-11-methyl-2,3,4,5-tetrahydro-8H-[1]benzothieno[3,2-f][1,2,4]-triazolo[4,3-a][1,4]-diazepine 2.8 ml (0.02 Mol) of triethylamine are added dropwise at 10° C. to 6.6 g (0.0165 Mol) of the compound of Example 18 and 1.55 ml (0.02 Mol) of methane sulfonic acid chloride in 60 ml of anhydrous methylene chloride; the reaction mixture is stirred for a further 2 hours at ambient temperature and the organic phase is then washed with water and dried. After removal of the solvent the oily residue is triturated with ethylacetate or ether and yields 7 g of yellowish crystals, m.p. 250° C. (yield 89%).

EXAMPLE 21

4-(N-Morpholinomethyl)-6-(2-chlorophenyl)-11-methyl-2,3,4,5-tetrahydro-8H-[1]benzothieno[3,2-f][1,2,4]triazolo[4,3-a][1,4]-diazepine 3.5 g (0.007 Mol) of the compound of Example 20 are suspended in 50 ml of dioxan, mixed with 3 g (0.035 Mol) of morpholine and refluxed for 8 hours. The solvent is removed from the resulting clear solution and the residue is distributed between 2N hydrochloric acid and methylene chloride. The aqueous phase is extracted with methylene chloride and then made alkaline. The precipitated base is extracted with methylene chloride, the organic phase is washed with water and dried. After removal of the solvent the residue is chromatograph on silica gel using methylene chloride/methanol 9:1 as eluant, the solid material obtained is crystallised from ethyl acetate and 1.9 g of crystals are obtained, m.p. 189°–190° C.

EXAMPLE 21a

3-Morpholin-4-yl-methyl)-5-(2-chlorophenyl)-10-methyl-3,4-dihydro-2H,7H-cyclopenta[4,5]thieno[3,2-f][1,2,4]triazolo[4,3-a][1,4]diazepine Starting from the compound described in Example 7b), namely 3-(ethoxycarbonyl)-5-(2-chlorophenyl)-10-methyl-3,4-dihydro-2H,7H-cyclopenta[4,5]thieno[3,2-f][1,2,4]triazolo[4,3-a][1,4]diazepine, the 3-hydroxymethyl compound of Example 65, m.p. 178°–180° C. (from isopropylether/ethyl acetate) is obtained in an 81% yield using sodium borohydride in tert.-butanol with methanol activation analogously to Example 18. It is converted analogously to Example 20 in a quantitative yield into the 3-methanesulfonyloxymethyl compound of Example 67, which occurs as an oil. Analogously to Example 21 the 3-(morpholin-4-yl-methyl) compound of example 66 can then be obtained in a 79% yield with an m.p. of 179°–181° C. (acetonitrile). This compound can be obtained completely free from organic solvents by dissolving in water at pH 4.1–5, briefly distilling off the aqueous solution in a water jet vacuum using a Rotavapor and subsequent precipitation by pH adjustment to pH 6.5–7 with saturated bicarbonate solution. M.p. 136°–138° C. (water).

EXAMPLE 22

3-(N-Phthalimidomethyl)-5-(2-chlorophenyl)-10-methyl-3,4-dihydro-2H,7H-cyclopenta[4,5]thieno[3,2-f][1,2,4]triazolo[4,3-a][1,4]diazepine 6 g (0.013 Mol) of 3-methanesulfonyloxymethyl-5-(2-chlorophenyl)-10-methyl-3,4-dihydro-2H,7H-cyclopenta[4,5]thieno[3,2-f][1,2,4]triazolo[4,3-a][1,4]-diazepine (prepared analogously to Example 20) and 2.4 g (0.013 Mol) of potassium phthalimide are stirred into 60 ml of anhydrous DMF (dimethylformamide) for 8 hours at 80° and, after cooling, stirred into 250 ml of water. After extractive working up with methylene chloride, the residue may be chromatographed on silica gel using methylene chloride/methanol 9:1 as eluant.

EXAMPLE 23

3-Aminomethyl-5-(2-chlorophenyl)-10-methyl-3,4-dihydro-2H,7H-cyclopenta[4,5]thieno[3,2-f][1,2,4]triazolo[4,3-a][1,4]-diazepine A mixture of 6.5 g (0.012 Mol) of the compound of Example 22, 2.9 ml (0.06 Mol) of hydrazine hydrate and 100 ml of ethanol is stirred for 6 hours at ambient temperature, forming a suspension. This is suction filtered, the filtrate is evaporated down, the residue is taken up in 2N hydrochloric acid and extracted with methylene chloride. The aqueous phase is then made alkaline and the base is extracted with methylene chloride, the organic phase is dried and the solvent is eliminated. The residue is chromatographed on silica gel using methylene chloride/methanol/ammonia 85:15:1 and yields 1.2 g (24% yield) of the title compound as an amorphous substance.

EXAMPLE 23a 4-(Aminomethyl)-6-(2-chlorophenyl)-11-methyl-2,3,4,5-tetrahydro-8H-[1]benzothieno-[3,2-f][1,2,4]triazolo[4,3-a][1,4]diazepine 4.3 g (9 mmol) of mesylate (Example 20, m.p. 250° C.) are stirred into 40 g of dimethylformamide, after the addition of 1 g of sodium azide, for 6 hours at 80°–100° C. The solvent is distilled off in vacuo, the residue is taken up in methylene chloride, washed with water, dried and evaporated down. The addition of ether yields 3.4 g of crystals of the corresponding azide, m.p. 175°–176° C. 3.2 g of these compounds are hydrogenated in the presence of Raney nickel in 60 ml of methanol. 2.1 g of colourless crystals are obtained, m.p. 115°–118° C. (decomp).

EXAMPLE 24

3-Acetylaminomethyl-5-(2-chlorophenyl)-10-methyl-3,4-dihydro-2H,7H-cyclopenta[4,5]thieno[3,2-f][1,2,4]triazolo[4,3-a][1,4]diazepine 0.2 g (0.0005 mol) of the compound of Example 23 and 0.07 ml (0.0005 mol) of triethylamine are dissolved in 10 ml of anhydrous methylene chloride, then mixed with 0.04 ml of acetyl chloride and stirred for one hour at ambient temperature. The reaction mixture is then washed with water and dried, the solvent is removed and the residue is chromatographed on silica gel using methylene chloride/methanol 9:1 as eluant. 0.1 g of the acetylamino compound is obtained as an amorphous substance in a 45% yield.

EXAMPLE 25

3-Thioacetyl-6-(2-chlorophenyl)-11-methyl-2,3,4,5-tetrahydro-8H-pyrido[4',3':4,5]thieno [3,2-f][1,2,4]triazolo[4,3-a][1,4]diazepine Starting from acetylpiperidone-4, analogously to Example 1, 2-amino-3-(2-chlorobenzoyl)-6-acetyl-4,5,6,7-tetrahydro-thieno[2,3-c]pyridine is obtained in a 62% yield and from this, in a quantitative yield, the 2-bromoacetylamino and 2-aminoacetylamino compounds are also obtained. Cyclisation to obtain the 5-(2-chlorophenyl)-8-acetyl-6,7,8,9-tetrahydro-1H,3H-pyrido[4',3':4,5]thieno[2,3-e][1,4]diazepin-2-one, m.p. 248°–250° C., succeeds with a 53% yield.

Reaction with phosphorous pentasulphide produces, in a 53% yield, 5-(2-chlorophenyl)-8-thioacetyl-6,7,8,9-tetrahydro-1H,3 H-pyrido[4',3':4,5]thieno[2,3-e][1,4]diazepin-2-thione (mass spectrum m/e=405/407), from which the desired compound is obtained in a 30% yield with a melting point of 250° C. (mass spectrum m/e=427/429) by the hydrazine hydratetriethylorthoacetate method.

EXAMPLE 26

6-(2-Chlorophenyl)-11-methyl-2,3,4,5-tetrahydro-8-H-pyrido[4',3':4,5]thieno[3,2-f][1,2,4] triazolo[4,3-a][1,4]diazepine 4.8 g (0.011 mol) of the compound of Example 25 and 100 ml of 2N methanolic potassium hydroxide solution are stirred for 1 hour at 60° C., producing a clear solution. After the solvent has been eliminated, the residue is distributed between methylene chloride and water and the methylene chloride phase is extracted with 2N hydrochloric acid. The hydrochloric acid phase is then made alkaline and the base precipitated is extracted with methylene chloride, the organic phase is washed with water and dried and the solvent is removed. The residue is chromatographed on silica gel using methylene chloride/methanol 9:1 as eluant. 2.6 g of the diazepine are obtained (63% yield) with an m.p. 84°–86° C.

EXAMPLE 27

3-(Carboethoxymethyl)-6-(2-chlorophenyl)-11-methyl-2,3,4,5-tetrahydro-8-H-pyrido[4',3':4,5]thieno[3,2-f][1,2,4] triazolo[4,3-a][1,4]diazepine 1.15 g (0.007 mol) of ethyl bromoacetate in 10 ml of anhydrous THF are added dropwise at ambient temperature to 2.1 g (0.0057 mol) of the compounds of Example 26 and 1 ml (0.007 mol) of triethylamine in 20 ml of anhydrous THF and the mixture is stirred for 48 hours. After filtration, the filtrate is evaporated down and the residue remaining is distributed between methylene chloride and water. The organic phase is washed with water and dried and the solvent is removed. The residue is chromatographed on silica gel using methylene chloride/methanol 9:1 as eluant and yields 1.6 g (62% yield) of the desired compound as an oil.

EXAMPLE 28

4-Carboethoxy-6-(2-chlorophenyl)-11-methyl-2,3,4,5-tetrahydro-8H-[1]benzothieno [3,2-f]imidazo[1,2-a][1,4]diazepine The hydrochloride is prepared from 2-propargylamino-5-(2-chlorophenyl)- 7-carboethoxy-6,7,8,9-tetrahydro-1H,3H-[1]benzothieno[2,3-e][1,4]diazepine, the intermediate compound of Example 10, by dissolving in acetonitrile and adding ethereal hydrochloric acid (yellow crystals, m.p. 240° C.).

13.7 g (0.029 mol) of this hydrochloride are stirred for 1 hour at 200° C., cooled and taken up in methylene chloride, washed with dilute ammonia and water and, after drying the solvent is removed. The residue is chromatographed on silica gel using methylene chloride/methanol as eluant and yields 3.6 g (29% yield) of the imidazodiazepine as an amorphous powder.

EXAMPLE 28a

3-Carbomethoxy-5-(2-chlorophenyl)-10-methyl-3,4-dihydro-2H,7H-cyclopenta[4,5] thieno[3,2-f]imidazo[1,2-a][1,4]diazepine 0.25 g (0.5 mmol) of 7-carbomethoxy-5-(2-chlorophenyl)-2-(2-methyl- 1,3-dioxolan-2-yl-amino)-7,8-dihydro-1H,3H,6H-cyclopenta[4,5]thieno[2,3-e][1,4]diazepine, the preparation of which is described in Example 10a, are cyclised to form the imidazo compound analogously to Example 10a. If concentrated ammonia is used instead of concentrated sodium hydroxide solution for the neutralisation, the carbomethoxy function may be obtained in the 7 position and 0.15 g of the title compound are isolated in a 70% yield.

$^1$H-NMR (CDCl$_3$) δ7.31–7.51 (m, 4H, aryl-H); 6.93 (qu, J<1 Hz, 1H, CH═); 4.15 (s, broad, 2H, CH$_2$-7 ring); 3.69 (s, 3H, OCH$_3$); 3.08–3.61 (m, 5H, CH$_2$, CH, 5-ring); 2.44 (d, J<1 Hz, 3H, CH$_3$—C═):

EXAMPLE 28b.

The compound 3-carbomethoxy-5-(2-chlorophenyl)-10-methyl-3,4-dihydro- 2H,7H-cyclopenta[4,5]thieno[3,2-f] imidazo[1,2-a][1,4]diazepine, obtained according to Example 28a or alternatively analogously to Example 28, is reduced analogously to Example 21a in a 90% yield to yield the 3-hydroxymethyl compound of Example 158, which occurs as a light coloured oil and is then converted, in an 87% yield, into the 3-methanesulphonyloxymethyl compound of Example 159, which occurs as a yellow oil. Further reaction with morpholine yields the amorphous compound of Example 113 in a 51% yield.

EXAMPLE 29

N-{6-(2-Chlorophenyl)2,3,4,5-tetrahydro-8H-[1] benzothieno[3,2-f][1,2,4]triazolo[4,3-a][1,4] diazepin-4(R,S)-yl]carbonyl}-S-leucine morpholide 3 g (7.25 mmol) of the racemic cyclohexane carboxylic acid described in Example 1 are stirred into a mixture of 55 ml of tetrahydrofuran and 20 ml of dimethyl formamide with 1.2 g (7.4 mmol) of carbonyldiimidazole for 1 hour at ambient temperature. Then. 1.8 g (7.6 mmol) of S-leucine morpholide hydrochloride and 0.77 g (7.6 mmol) of triethylamine are added. The reaction mixture is stirred for 3 days, evaporated down in vacuo, the residue is taken up in dichloromethane and extracted several times with water. The organic phase is concentrated by evaporation after drying and the residue remaining is separated into the two diastereomers by chromatography on silica gel RP 18 using an eluant system of acetonitrile: 0.01 molar ammonium carbonate solution: diethylamine (35:65:0.1).

The first fraction is crystallised with ether, after evaporation of the solvents.

Yield 90 mg (2%), m.p. 158°–160° C.

$C_{30}H_{55}ClN_6O_3S \times H_2O$ (613.18) Calculated: C 58.76 H 6.08 N 13.71 Found: C 58.27 H 582 N 13.46

The second fraction is also crystallised from ether Yield: 80 mg (2%), m.p. 162°–165° C.

$C_{30}H_{35}ClN_6O_3 \times 0.5\ H_2O$ (604.17) Calculated: C 59.64 H 6.01 N 13.91 Cl 5.87 S 5.31 Found: C 59.65 H 6.04 N 13.80 C15.73 S 5.36

EXAMPLE 30

4-[4,4-Dimethyl-2-oxazolin-2-yl]-2,3,4,5-tetrahydro-8H-[1]benzothieno[3,2-f][1,2,4]triazolo[4,3-a][1,4]diazepine 2.05 g (5 mmol) of the cyclohexane carboxylic acid from Example 1 are combined with 0.45 g (5 mmol) of 2-amino-2-methyl-1-propanol, 1.52 g (15 mmol) of triethylamine and 3.1 g of carbon tetrachloride in a mixture of 10 ml of pyridine:acetonitrile (1:1). Within 3 hours, 3.9 g (15 mmol) of triphenylphosphine dissolved in 10 ml of pyridine/acetonitrile (1:1) are added dropwise at ambient temperature. To complete the reaction the mixture is stirred for a further 12 hours. The suspension is concentrated by evaporation. The residue is suspended first in ether and then in ethyl acetate and filtered off each time. The filtrates are combined and evaporated to dryness. The residue is purified by chromatography on silica gel using dichloromethane/methanol 95:5. The clean fractions are concentrated and then recrystallised from ether.

Yield: 0.9 g (39%), m.p. 239° C.

$C_{24}H_{24}ClN_5OS$ (466.01) Calculated: C 61.85 H 5.19 N 15.03 Cl 7.61 S 6.88 Found: C 61.76 H 5.31 N 14.75 Cl 7.60 S 6.86

The compound mentioned in the title is also obtainable by the following method.

1 g (2.1 mmol) of the carboxylic acid amide 42 from Table 1 is combined with 1 ml of thionyl chloride in 50 ml of dichloromethane whilst cooling with ice. After 5 hours at ambient temperature the suspension is concentrated by evaporation, the residue is mixed with ice water, made alkaline and extracted with dichloromethane. 0.41 g (43%) of the title compound, m.p. 239° C., are obtained from the organic phase as described above.

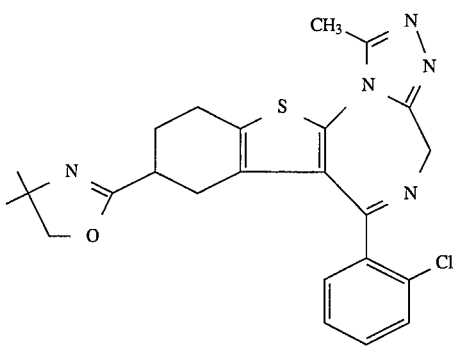

EXAMPLE 31

4-[4,4-Dimethyl-2-oxazolin-2-yl]-2,3,4,5,6,7-hexahydro-8H-[1]benzothieno[3,2-f][1,2,4]triazolo[4,3-a][1,4]diazepine 2 g (4.1 mmol) of the primary carboxylic acid amide 42 from Table 1 are reduced in a mixture of 12 ml of glacial acetic acid and 12 ml of dichloromethane by the addition of 1 g of zinc powder. After 3 hours' stirring at ambient temperature, it is filtered off, washed with dichloromethane and the combined filtrates are made alkaline with ammonia solution. The organic phase is separated off, dried and concentrated by evaporation. The residue is purified by chromatography on silica gel (eluant: dichloromethane/methanol 95/5). The analytically pure substance is obtained in crystalline form from ether: 0.4 g, m.p. 190° C.

The amide thus prepared is converted into the oxazoline mentioned in the title by the reaction of cyclisation with thionyl chloride described in Example 30.

70 mg are obtained, m.p. 179° C.

EXAMPLE 32

4-Cyano-6-(2-chlorophenyl)-2,3,4,5-tetrahydro-8H-[1]benzothieno[3,2-f][1,2,4]triazolo[4,3-a][1,4]diazepine 10.3 g (25 mmol) of the primary carboxylic acid amide 44 from Table 1 are suspended in 150 ml of dichloroethane and 9 ml of phosphorous oxychloride and refluxed for 5 hours. The reaction mixture is cooled, poured onto ice, made alkaline and extracted with dichloromethane. After purification by chromatography on silica gel using dichloromethane/methanol (95/5) and recrystallisation from ethyl acetate/ether, 7.6 g (78%) of the cyanide are obtained from the organic phase, m.p. 212° C.

$C_{20}H_{16}ClN_5S$ (393.89) Calculated: C 60.98 H 4.09 N 17.78 Cl 9.00 Found: C 60.93 H 4.07 N 17.71 Cl 9.16

EXAMPLE 33

4-[2-Imidazolin-2-yl]-6-(2-chlorophenyl)-2,3,4,5-tetrahydro-8H-[1]benzothieno[3,2-f][1,2,4]triazolo[4,3-a][1,4]diazepine 3.4 g (8.6 mmol) of the cyanide mentioned in Example 32 are mixed with 8 ml of a 30% ethanolic hydrochloric acid and left to stand for 10 days in a refrigerator. The imido ester hydrochloride precipitated is filtered off. The crude product is immediately reacted further. Whilst cooling with ice, 10 ml of ethylene diamine are added dropwise and the mixture is heated for 20 hours at 80° C. After evaporation of the excess amine, the residue is taken up in ice water, adjusted to pH 3, washed with dichloromethane and the organic phase is discarded. Then the aqueous phase is made strongly alkaline and extracted once more with dichloromethane. The latter organic phase is brought to dryness and the residue is chromatographed on basic aluminium oxide with dichloromethane/methanol 97/3. The title compound is isolated as the first fraction. By recrystallising from ethyl acetate/ether, 1.2 g (34%) of the imidazoline are obtained, m.p. 230° C.

$C_{22}H_{21}ClN_6$ (436.96)

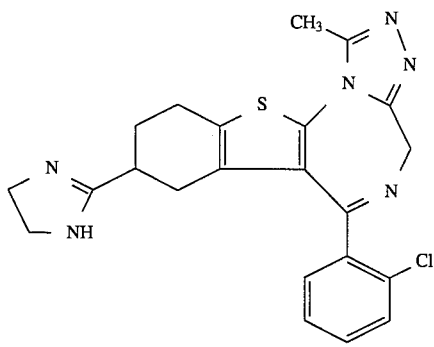

Calculated: C 60.47 H 4.84 N 19.23 Cl 8.11 S 7.34 Found: C 60.52 H 4.80 N 19.23 Cl 8.09 S 7.24

The acid amide 43 in Table 1 is obtained as the second fraction in a yield of 1.1 g.

EXAMPLE 33a

4-[4,4-Dimethylimidazolin-2-yl]-6-(2-chlorophenyl)-2,3,4,5-tetrahydro-8H-[1]benzothieno[3,2-f][1,2,4]triazolo[4,3-a][1,4]diazepine 17.6 g (44.7 mmol) of the nitrile of Example 32 are dissolved in a mixture of 100 ml of ether and 100 ml of ethanol, dried hydrochloric acid gas is passed through the solution for 2 hours and it is then left to stand for 2 days whilst remaining thoroughly sealed. The solvent is evaporated down and 20 g of 1,2-diamino-2-methylpropane and 30 ml of ethanol are added to the crude imido ester product. After heating to 80° C. for 3 hours the product is worked up as in Example 33.

In this way, 13.3 g (64% of theory) of the title compound are obtained, m.p. 272° C. (ethanol/ether).

Calculated: C. 61.99 H 5.42 N 18.07 Cl 7.62 S 6.90 Found: C 61.66 H 5.46 N 18.00 Cl 7.56 S 6.55

EXAMPLE 34

4-[1-Methyl-2-imidazolin-2-yl]-6-(2-chlorophenyl)-2,3,4,5-tetrahydro-8H-[1]benzothieno[3,2-f][1,2,4]triazolo [4,3-a][1,4]diazepine 0.65 g (1.5 mmol of the imidazoline obtained in Example 33 are dissolved in 40 ml of tetrahydrofuran with the addition of 5 ml of dimethyl formamide. 0.08 g of sodium hydride (80% dispersion in oil) are added and the mixture is stirred for 30 minutes at ambient temperature. Then 0.1 ml (1.6 mmol) of methyl iodide dissolved in 10 ml of tetrahydrofuran are added dropwise. After 24 hours the mixture is evaporated down and the residue is chromatographed on basic aluminium oxide as described above.

In this way 0.2 g (29%) of the N-methyl-imidazoline compound are obtained, m.p. 195°–197° C., as a hemihydrate.

$C_{23}H_{23}ClN_6S×½ H_2O$ (460) Calculated: C 60.05 H 5.26 N 18.27 Cl 7.71 S 6.97 Found: C 60.30 H 5.11 N 18.25 Cl 7.78 S 7.08

EXAMPLE 34a

4-Amino-6-(2-chlorophenyl)-11-methyl-2,3,4,5-tetrahydro-8H-[1]benzothieno[3,2-f][1,2,4]triazolo[4,3-a][1,4]diazepine 10.3 g (25 mmol) of the cyclohexane carboxylic acid of Example 1 are placed in 50 ml of acetone and then at 0° C. 4.2 ml of triethylamine and 3.6 g of ethyl chloroformate are successively added dropwise. The mixture is stirred for 45 minutes at this temperature and 1.75 g (27 mmol) of sodium azide dissolved in 10 ml of water are added dropwise. The mixture is then allowed to react for 2 hours at 10° C., the acetone is largely removed, the residue is mixed with water and extracted with dichloromethane. After the organic phase has been dried and concentrated in vacuo, 11.8 g of carboxylic acid azide are obtained as an amorphous powder.

1 g of this crude product is heated in 15 ml of anhydrous dioxan for 3 hours under reflux conditions, then 50 ml of 0.1N HCl are added, the mixture is heated for a further 3 hours, concentrated by evaporation, adjusted to pH 12 with sodium hydroxide solution and left to stand for 2 hours. Then the amine is extracted with dichloromethane and, after evaporation of the organic phase, chromatographed on basic aluminium oxide using as eluant dichloromethane and methanol (97:3).

0.1 g of the amine is isolated as an amorphous substance, m.p. 180°–185° C.

$^1$H-NMR (CDCl$_3$) δ7.10–7.68 (4H, m, aryl-H); 5.57 and 4.20 (2H, AB-system, $J_{AB}$=13 Hz, CH$_2$-7 ring); 2.67 (3H, s, CH$_3$-triazole ring); 1.29–3.29 (9H, m, cyclohexane ring, NH$_2$).

EXAMPLE 34b

4-Methoxycarbonylamino-6-(2-chlorophenyl)-11-methyl-2,3,4,5-tetrahydro-8H-[1]benzothieno[3,2-f][1,2,4]triazolo [4,3-a][1,4]diazepine 1.1 g (2.7 mmol) of the isocyanate obtained in the above Example are stirred together with 20 ml (0.5 mol) of methanol and 20 ml of dichloromethane and 0.2 g (1.8 mmol) of DABCO (1,4-diazabicyclo(2,2,2)octane) for 3 days at ambient temperature. The mixture is evaporated to dryness and purified by chromatography on silica gel using dichloromethane/methanol 95:5 as eluant. The clean fractions are recrystallised from ether.

Yield: 0.3 g (40%) m.p. 166°–168° C.

$^1$H-NMR (CDCl$_3$) δ7.3 (4H, m, aryl-H), 5.57 and 4.2 (2H, AB-system, $J_{AB}$=13 Hz, CH$_2$-7 ring), 3.6 (5.3H, CH$_3$O—) 2.77 (m, 2H) and 1.77–2.22 (m, 5H, cyclohexane-H), 2.66 (3H, s, CH$_3$-triazole). m/e=441/443 (M$^+$), 409/411 (M$^+$-32(OCH$_3$)), 366/368 (M$^+$-75 (NH$_2$COOCH$_3$)).

In the Tables which follow, some additional abbreviations are used: Me=methyl, Et=ethyl, i-Pr=isopropyl, t-Bu=tert. butyl.

The numbering given in the Examples refers to that shown in the following structures:

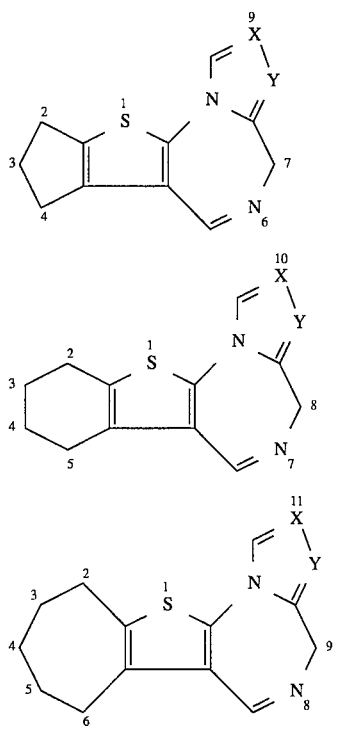

Using the methods described hereinbefore, the following compounds may be obtained:

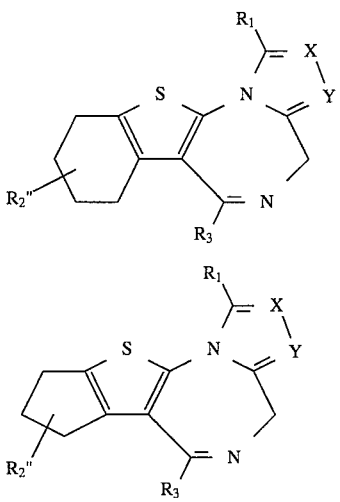

unless otherwise stated, X and Y both represent nitrogen and $R_3$=o-chlorophenyl.

| Ex. | $R^*_2$ | $R_1$ | Type | Pos. | according to Example | m.p. |
|---|---|---|---|---|---|---|
| 35 | $-CO-N(C_2H_5)_2$ | $CH_3$ | A | 3 | 2 | 226–228° C. |
| 36 | $-CO-N(C_2H_5)_2$ | $CH_3$ | A | 4 | 1 | 206–209° C. |
| 37 | $-CO-N\diagup\diagdown N-CH_3$ | $CH_3$ | A | 4 | 1 | 253–255° C. |
| 38 | $HO-(CH_2)_2-\underset{\underset{CH_3}{\|}}{N}-CO-$ | $CH_3$ | A | 4 | 1 | 250–251° C. |
| 39 | $HO-\underset{\underset{CH_3}{\|}}{\overset{\overset{CH_3}{\|}}{C}}-(CH_2)_2-\underset{}{\overset{H}{N}}-CO-$ | $CH_3$ | A | 4 | 1 | 237–238° C. |
| 40 | $(C_2H_5)_2N-(CH_2)_2-\overset{H}{N}-CO-$ | $CH_3$ | A | 4 | 1 | powder |
| 41 | $O_2N-\underset{\underset{CH_3}{\|}}{\overset{\overset{CH_3}{\|}}{C}}-(CH_2)_2-\overset{H}{N}-CO-$ | $CH_3$ | A | 3 | 2 | powder |
| 42 | $HO-CH_2-\underset{\underset{CH_3}{\diagdown}}{\overset{\overset{CH_3}{\diagup}}{C}}-\overset{H}{N}-CO$ | $CH_3$ | A | 4 | 1 | 198° C. |
| 43 | $H_2N-CH_2-CH_2-\overset{H}{N}-CO-$ | $CH_3$ | A | 4 | 1 | 223–224° C. |
| 44 | $H_2N-CO-$ | $CH_3$ | A | 4 |  | 280° C. |

-continued

| Ex. | R*₂ | R₁ | Type | Pos. | according to Example | m.p. |
|---|---|---|---|---|---|---|
| 45 | CH₃-CH(O-)-CH₂-N(-CO-)-CH₂-CH(CH₃)- (morpholine with 2,6-dimethyl) | CH₃ | A | 4 | 1 | 230–231° C. |
| 46 | (CH₃)₂N—CO— | CH₃ | B | 4 | 8 | 317–318° C. |
| 47 | (C₂H₅)₂N—CO— | CH₃ | B | 4 | 8 | 251–253° C. |
| 48 | (C₂H₅)₂N—CO— | CH₃ | B | 3 | 7 | powder |
| 49 | morpholino-CO— | —OCH₃ | B | 3 | 7/6 | powder |
| 50 | morpholino-CO— | —OCH₃ | B | 4 | 8/6 | 244–246° C. |
| 51 | morpholino-CO— | —OCH₃ | A | 4 | 6 | 207–209° C. |
| 52 | morpholino-CO— | H | A | 4 | 3 | 147–148° C. |
| 53 | 2,6-dimethylmorpholino-CO— | —OCH₃ | B | 3 | 7/6 | powder |
| 54 | morpholino-CO— | H | B | 4 | | 270–271° C. |
| 55 | morpholino-CO— | Br | B | 4 | | 280–282° C. |
| 56 | morpholino-CO— | H | B | 3 | | |
| 57 | morpholino-CO— | Br | B | 3 | | 120° C. (decomp) |

-continued

| Ex. | R*₂ | R₁ | Type | Pos. | according to Example | m.p. |
|---|---|---|---|---|---|---|
| 58 | O(CH₂CH₂)₂N—CO—CH₂—N(H)—CO— | CH₃ | B | 3 | 7 | powder |
| 59 | (2,6-dimethylmorpholino)—N—CO— | CH₃ | B | 3 | | powder |
| 60 | 4,5-dihydrothiazol-2-yl—NHCO— | CH₃ | A | 4 | 1 | 267–268° C. |
| 61 | 4-methylthiazol-2-yl—NHCO— | CH₃ | A | 4 | 1 | 318° C. |
| 62 | —CH₂—O—C(=O)—CH₃ | CH₃ | A | 4 | | 183–185° C. |
| 63 | —CH₂—N(1,2,4-triazol-1-yl) | CH₃ | A, X=CH | 4 | | 82° C. (decomp) |
| 64 | —CH₂—OH | CH₃ | A | 4 | | amorph |
| 65 | —CH₂—OH | CH₃ | B | 3 | | 95° C. (decomp) |
| 66 | —CH₂—N(morpholino) | CH₃ | B | 3 | | 177–178° C. |
| 67 | —CH₂—OSO₂—CH₃ | CH₃ | B | 3 | | oil |
| 68 | —CH₂—O—C(=O)—CH₃ | —H | B | 3 | | 161–162° C. |
| 69 | —CH₂—OSO₂CH₃ | —H | B | 3 | | 163–165° C. |
| 70 | —CH₂—N(morpholino) | —H | B | 3 | | 162–163° C. |
| 71 | —CH₂—N(C₂H₅)₂ | —H | B | 3 | | 430–433° C. |
| 72 | —CH₂—N(2,6-dimethylmorpholino) | —CH₃ | B | 3 | | 175—175° |
| 73 | —CH₂—N(morpholino) | —Br | B | 3 | | — |

-continued

| Ex. | R*₂ | R₁ | Type | Pos. | according to Example | m.p. |
|---|---|---|---|---|---|---|
| 74 | −CH₂−N(morpholine) | −OCH₃ | B | 3 | | − |
| 75 | CH₂−N(C₂H₅)₂ | Br | B | 3 | | − |
| 76 | −CH₂−N(C₂H₅)₂ | OCH₃ | B | 3 | | − |
| 77 | −CH₂−N(C₂H₅)₂ | CH₃ | B | 3 | | amorph |
| 78 | CH₂−N(Me)(iPr) | CH₃ | B | 3 | | amorph |
| 79 | (oxazine) | CH₃ | A | 4 | | 213 |
| 80* | (oxazine-CH₃) | CH₃ | A | 4 | | 212–213° C. |
| 81* | (oxazine-CH₃) | CH₃ | A | 4 | | 225–226 |
| 82 | (oxazine-(CH₃)₂) | CH₃ | B | 3 | | 228–229° C. |
| 83 | (imidazoline-(CH₃)₂, NH) | CH₃ | A | 4 | | 272° C. |
| 84 | (imidazoline-(CH₃)₂, N-CH₃) | CH₃ | A | 4 | | 215–217° C. |
| 85* | (oxazine-CH(CH₃)₂) | CH₃ | A | 4 | | 197–200° C. |

"Aza compounds"
86   3-Acetylaminomethylcarbonyl-6-(2-chlorophenyl)-11-methyl-2,3,4,5-tetrahydro-8H-        Oil -continued

| Ex. | R*₂ | R₁ | Type | Pos. | according to Example | m.p. |
|---|---|---|---|---|---|---|
| 87 | 3-(N-Morpholinocarbonylmethyl)-6-(2-chlorophenyl)-11-methyl-2,3,4,5-tetrahydro-8H-pyrido[4',3':4,5]thieno[3,2-f][1,2,4]triazolo[4,3-a][1,4]diazepine | | | | | 125–128° C. |

*Mixture of diastereomers (50:50)

| Ex. | R*₂ | R₁ | Type | Pos. | according to Example | m.p. |
|---|---|---|---|---|---|---|
| 88 | (2-imidazoline, N-H) | CH₃ | A | 4 | 4 | 250–252° C. |
| 89 | —C(O)—NHiPr | CH₃ | A | 4 | 1 | 280° C. |
| 90 | —C(O)—N(iPr)₂ | CH₃ | A | 4 | 1 | 209° C. |
| 91 | —C(O)—NHC(CH₃)₃ | CH₃ | A | 4 | 1 | 273° C. |
| 92 | (imidazoline with gem-diCH₃, N-H) | CH₃ | A | 4 | 4 | 257° C. |
| 93 | (tetrahydropyrimidine, N-CH₃) | CH₃ | A | 4 | 4 | 197° C. |
| 94 | (imidazoline with gem-diCH₃, N-iPr) | CH₃ | A | 4 | 4 | 206° C. |
| 95 | (tetrahydropyrimidine with gem-diCH₃, N-H) | CH₃ | A | 4 | 4 | 212–213° C. |
| 96 | (imidazoline, N-iPr) | CH₃ | A | 4 | 4 | 186° C. |
| 97 | (imidazoline, N-Et) | CH₃ | A | 4 | 4 | 198–199° C. |
| 98 | —C(O)—NH—(CH₂)₂—NH—Et | CH₃ | A | by-product of 97 | | 166–167° C. |

-continued

| Ex. | R*₂ | R₁ | Type | Pos. | according to Example | m.p. |
|---|---|---|---|---|---|---|
| 99 | N=C(N(CH₂)₃—CH₃)—N(H)—(CH₂)₃—CH₃ | CH₃ | A | 4 | 4 | amorph Hydrate 80–85° C. |
| 100 | 2-benzimidazolyl (NH) | CH₃ | A | 4 | 4 | 319° C. |
| 101 | —C(O)—NHC(CH₃)₃ | CH₃ | A<br>x = CH | 4 | | 278° C. |
| 102 | —C(O)—N(CH₂CH₂OCH₃)₂ | CH₃ | A<br>X = CH | 4 | 1 | amorph |
| 103 | —C(O)—N(CH₂CH₂OCH₃)₂ | CH₃ | A | 4 | 1 | amorph |
| 104 | —C(O)—NH—C₆H₅ | CH₃ | A | 4 | | 270° C. |
| 105 | —CH₂—NH—Et | CH₃ | B | 3 | | oil |
| 106 | —CH₂—N(Et)—C(O)CH₃ | CH₃ | B | 3 | | amorph |
| 107 | —CH₂—NH—CH₂—CH₂—NMe₂ × 2HCl | CH₃ | B | 3 | | amorph |
| 108 | —CH₂—NH—CH₂—CH₂—N(morpholino) | CH₃ | B | 3 | | oil |
| 109 | —CH₂—N(C(O)CH₃)—CH₂—CH₂—NMe₂ | CH₃ | B | 3 | | amorph |
| 110 | —CH₂—N(C(O)CH₃)—CH₂—CH₂—N(morpholino) | CH₃ | B | 3 | | amorph |
| 111 | —CH₂—N(piperazinyl-NH) | CH₃ | B | 3 | | oil |
| 112 | —CH₂—O—C(O)—CH₃ | CH₃ | B<br>X = CH | 3 | | oil |
| 113 | —CH₂—N(morpholino) | CH₃ | B<br>X = CH | 3 | | amorph |

-continued

| Ex. | R*₂ | R₁ | Type | Pos. | according to Example | m.p. |
|---|---|---|---|---|---|---|
| 114 | —CH₂—N(Et)₂ | CH₃ | B, X=CH | 3 | | oil |
| 115 | —CH₂—NH—(CH₂)₂—(1H-indol-3-yl) | CH₃ | B | 3 | | amorph |
| 116 | —CH₂—OCH₃ | CH₃ | B | 3 | | |
| 117 | —CH₂—O—C₆H₅ | CH₃ | B | 3 | | oil |
| 118 | —COOCH₃  R₃ = C₆H₅ | CH₃ | B | 3 | | 180° C. |
| 119 | —CH₂—OH  R₃ = C₆H₅ | CH₃ | B | 3 | | 235–236° C. |
| 120 | —CH₂—N(morpholino)  R₃ = C₆H₅ | CH₃ | B | 3 | | 205–207° C. |
| 121 | —CH₂—O—(benzo[1,3]dioxol-yl) | CH₃ | B | 3 | | 206–207° C. |
| 122 | —CH₂—O—(pyridin-3-yl) | CH₃ | B | 3 | | 200–205° C. |
| 123 | —CH₂—N(imidazol-1-yl) | CH₃ | B | 3 | | 222–225° C. |
| 124 | —CH₂—N(1,2,4-triazol-1-yl) | CH₃ | B | 3 | | 205–210° C. |
| 125 | —CH₂—S—(1,2,4-triazol-3-yl) | CH₃ | B | 3 | | oil |
| 126 | —CH₂—Br | CH₃ | B | 3 | | oil |
| 127 | —CH₂—CN | CH₃ | B | 3 | | 227–230° |
| 128 | —OH | CH₃ | A | 3 | 16 | 144–146° C. |
| 129 | —CH₂O—C(=O)—CH₃ | CH₃ | A | 3 | | 179–182° C. |
| 130 | —CH₂—N(morpholino) | CH₃ | A | 3 | | oil |
| 131 | —CH₂—OH | CH₃ | A | 3 | | amorph |
| 132 | —CON(C₃H₇)₂ | CH₃ | A | 3 | | 224–226° |
| 133 | —CON(CH₂—CH=CH₂)₂ | CH₃ | A, X=CH | 4 | | oil |

-continued

| Ex. | R*₂ | R₁ | Type | Pos. | according to Example | m.p. |
|---|---|---|---|---|---|---|
| 134 | —CON(C₃H₇)₂ | CH₃ | A<br>X=CH | 4 | | oil |
| 135 | *CON(CH₂—CH=CH₂)₂ | CH₃ | A | 4 | | oil |
| 136 | —CON⟨NO⟩ | CH₂Cl | A | 4 | | 240° |
| 137 | —CON⟨NO⟩ | CH₂OH | A | 4 | | 242° |
| 138 | —CON(CH₂—CH=CH₂)₂ | CH₃ | B | 3 | | amorph |
| 139 | —CON[(CH₂)₇CH₃]₂ | CH₃ | B | 3 | | oil |
| 140 | —CON(C₃H₇)₂ | CH₃ | B | 3 | | oil |
| 141 | —CON(C₃H₇)₂ | CH₃ | B<br>X=CH | 3 | | oil |
| 142 | —CON(CH₂—CH=CH₂)₂ | CH₃ | B<br>X=CH | 3 | | oil |
| 143 | —CO—N⟨NO⟩ | CH₃ | B<br>X=CH | 3 | | decomp at 95 |
| 144 | —CO—N⟨NO⟩ | Br | B<br>X=CH | 3 | | decomp at 135 |
| 145 | —CO—N⟨NO⟩ | H | B<br>X=C—CH₃ | 3 | | decomp at 85 |
| 146 | —CO—N⟨NO⟩ | CH₃ | B<br>X=CH | 3 | | 130–131° |
| 147 | —CON(H)—(CH₂)₁₅—CH₃ | CH₃ | B | 3 | | oil |
| 148 | —CH₂—COOH | CH₃ | B | 3 | | 233–234° C. |
| 149 | —CH₂—C(=O)—N⟨NO⟩ | CH₃ | B | 3 | | amorph. |
| 150 | —CH₂—CH₂—OH | CH₃ | B | 3 | | |
| 151 | —CH₂—CH₂—O—SO₂CH₃ | CH₃ | B | 3 | | |
| 152 | —CH₂—CH₂—N⟨NO⟩ | CH₃ | B | 3 | | |
| 153 | —CH₂—CH₂—N⟨imidazole⟩ | CH₃ | B | 3 | | |
| 154 | —CH₂—COOMe | CH₃ | B | 3 | | |
| 155 | —CH₂—NH-n-C₁₈H₃₇ | CH₃ | B | 3 | | |
| 156 | —CH₂—O—C(=O)-n-C₁₇H₃₅ | CH₃ | B | 3 | | oil |
| 157 | —CH₂—O-n-C₁₈H₃₇ | CH₃ | B | 3 | | |
| 158 | CH₂—OH | CH₃ | B<br>X=CH | 3 | | light oil |

| Ex. | R*₂ | R₁ | Type | Pos. | according to Example | m.p. |
|---|---|---|---|---|---|---|
| 159 | —CH₂—O—SO₂CH₃ | CH₃ | B X = CH | 3 | | yellow oil |
| 160 | Metachlorophenyl-NH—CO— | CH₃ | B | 3 | | 285° C. |

TABLE II

Intermediate compounds of general formula

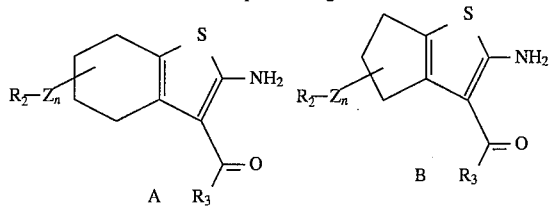

| Ex. | Z$_n$ | R₂ | R₁ | Type | Pos. | according to Example | m.p. |
|---|---|---|---|---|---|---|---|
| 1. | — | —COOCH₃ | Cl | B | 5 | | 121–122° |
| 2. | —CH₂— | —OH | Cl | B | 5 | from 1 with LiAlH₄ | amorph |
| 3. | —CH₂— | —OSO₂—CH₃ | Cl | B | 5 | | oil |
| 4. | —CH₂— | —N(morpholine) | Cl | B | 5 | | 184–186° |
| 5. | — | —COOCH₃ | O | B | 5 | | 133–135° |
| 6. | — | —COOCH₃ | Cl | A | 5 | | 136–137° |
| 7. | — | —COOCH₃ | Cl | A | 6 | | 167–168° |
| 8. | — | —C(=O)—N(morpholine) | Cl | A | 5 | | |
| 9. | — | —C(=O)—N((CH₂)₂CH₃)₂ | Cl | B | 5 | | |

The following Table lists the ¹H-NMR spectra of some compounds.

Table II: ¹H-NMR spectra:

EXAMPLE 19

¹H-NMR (CDCl₃): δ7.17–7.56 (m, 4H-aryl); 4.94 (s, broad, CH₂-7 ring); 3.98/d, J=6 Hz, 2H, OCH₂); 1.93–3.33 (m, 5H, 5-ring); 2.70 (s, 3H, CH₃-triazole); 2.02 (s, 3H, CH₃C=O).

EXAMPLE 20

¹H-NMR (CDCl₃): δ7.18–7.62 (m, 4H, aryl-H); 5.59, 4.22 (AB-system, J$_{AB}$=13 Hz, 2H, CH₂-7 ring); 3.98 (d, J=5 Hz, 2H, CH₂); 2.92 (S, 3H, CH₃—SO₂); 2.69 (s, 3H, CH₃ triazole); 1.31–3.00 (m, 7H, CH₂, CH, 6-ring)

EXAMPLE 22

¹H-NMR (CDCl₃): δ7.62–7.91 (m, 4H, aryl-phthalimide); 7.18–7.56 (m, 4H, aryl-H); 4.92 (broad, 2H, CH₂-7 ring); 4.13 (d, J=6 Hz, 2H, NCH₂); 2.69 (s, 3H, CH₃ triazole ring); 1.60–3.33 (m, 5H, CH₂, CH, 5-ring).

EXAMPLE 23

¹H-NMR (CDCl₃): δ7.20–7.58 (m, 4H, aryl-H); 4.92 (s, broad, 2H, CH₂-7 ring); 2.69 (s, 3H, CH₃-triazole ring); 1.71 (s, 2H, NH₂); 1.56–3.20 (m, 7H, CH₂, CH-5-ring, N—CH₂).

EXAMPLE 24

¹H-NMR (CDCl₃): δ7.22–7.56 (m, 4H, aryl); 5.73 (t, J=6 Hz, 1H, NH); 4.91 (s, broad, 2H, CH₂-7-ring; 3.22 (m, 2H, N—CH₂); 2.68 (s, 3H, CH₃ triazole-ring); 1.94 (s, 3H, CH₃ (=O); 1.89–3.09 (m, 5H, CH₂, CH, 5-ring).

EXAMPLE 27

¹H-NMR (CDCl₃): δ7.18–7.55 (m, 4H, aryl-H); 5.54/4.22 (2 s, broad, 2H, CH₂-7-ring); 4.22 (qu, J=7 Hz, 2H, OCH₂); 3.91 (s, 2H, N—CH₂C=C); 3.43 (s, 2H, N—CH₂C=O); 2.78 (m, 2H, NCH₂CH₂); 2.70 (s, 3H, CH₃ triazole); 1.98 (m, 2H, N—CH₂CH₂); 1.30 (t, J=7 Hz, CH₃CH₃—).

EXAMPLE 28

¹H-NMR (CDCl₃): δ7.04–7.67 (m, 4H, aryl); 6.87 (qu, J=<1 Hz, 1H, CH=); 5.38 and 4.07 (AB-system, J$_{AB}$=13 Hz, 2H, CH$_2$-7 ring); 4.06 (qu, J=8 Hz, 2H, OCH$_2$); 2.41 (d, J=<1 Hz, 3H, CH$_3$—C=); 1.48–3.07 (m, 7H, CH$_2$, CH-6-ring); 1.17 (t, J=8 Hz, CH$_2$CH$_3$).

EXAMPLE 64

$^1$H-NMR (CDCl$_3$); δ7.17–7.64 (m, 4H, aryl-H); 6.87 (qu, J<1 Hz, 1H, HC=); 5.37/4.09 (AB system, J$_{AB}$=12 Hz, 2H, CH$_2$-7 ring); 3.37 (d, J=6 Hz, 2H, CH$_2$); 2.41 (d, J=<1 Hz, 3H, CH$_3$ imidazole ring); 1.04–2.86 (m, 7H, CH$_2$, CH, 6-ring).

EXAMPLE 67

$^1$H-NMR (CDCl$_3$): δ7.22–7.63 (m, 4H, aryl-H); 4.97 (s, broad, 2H, CH$_2$-7 ring); 4.12 (d, J=6 Hz, 2H, OCH$_2$); 2.98 (s, 3H, CH$_3$—SO$_2$—); 2.76 (s, 3H, CH$_3$ triazole ring); 1.58–3.37 (m, 5H, CH$_2$, CH-5 ring).

EXAMPLE 74

$^1$H-NMR (CDCl$_3$) δ7.25–7.48 (4H, m, aryl-H); 4.85 (2H, AB system J$_{AB}$=12 Hz, CH$_2$-7 ring); 4.28 (3H, s, OCH$_3$); 3.64 (4H, m OCH$_2$ morpholinyl); 2.35 (4H, m, NCH$_2$ morpholinyl); 1.43–3.28 (7H, m, cyclopentenyl-H, N—CH$_2$).

EXAMPLE 77

$^1$H-NMR (CDCl$_3$); δ7.19–7.60 (m, 4H, aryl-H); 4.92 (s, broad, 2H, CH$_2$-7 ring); 2.70 (s, 3H, CH$_3$ triazole); 2.47 (qu, J=7 Hz, 4H, N—(CH$_2$)$_2$), 1.47–3.18 (m, 7H, CH$_2$, CH-5 ring, NCH$_2$); 0.93 (t, J=7 Hz, 6H (CH$_3$—CH$_2$)$_2$—N).

EXAMPLE 78

$^1$H-NMR (CDCl$_3$) δ7.20–7.54 (4H, m, aryl-H); 4.92 (2H, s, broad, CH$_2$-7 ring); 2.68 (3H, s, CH$_3$C=N); 2.15 (3H, s, CH$_3$N); 1.46–3.24 (8H, m, H-cyclopentenyl, N—CH); 0.92 (6H, 2d, J=7 Hz, CH$_3$-isopropyl).

EXAMPLE 86

$^1$H-NMR (CDCl$_3$): δ7.23–7.62 (m, 4H, aryl-H); 6.56 (t, J=4 Hz, $^1$H, NH); 5.62/4.31 (AB-system, broad, 2H, CH$_a$-7 ring); 4.67 (s, 2H, NCH$_2$-thiophene); 4.07 (d, J=4 Hz, 2H, CH$_2$NH); 3.51 (s, broad, 4H, CH$_2$ 6-ring); 2.70 (s, 3H, CH$_3$ triazole); 2.06 (s, 3H, CH$_3$C=O).

EXAMPLE 105

$^1$H-NMR (CDCl$_3$) δ7.18–7.59 (4H, m, aryl-H); 4.93 (2H, s, broad, CH$_2$-7 ring); 2.69 (3H, s, CH$_3$—C=N); 2.61 (2H, qu, J=7 Hz, CH$_3$CH$_2$—N); 1.44–3.29 (8H, m, H-cyclopentenyl, NH); 1.05 (3H, t, J=7 Hz, CH$_3$CH$_2$—N).

EXAMPLE 106

$^1$H-NMR (CDCl$_3$) δ7.22–7.56 (4H, m, aryl-H); 4.93 (2H, s, broad, CH$_2$-7 ring); 2.68 (3H, s, CH$_3$C=N); 2.06 (3H, s, CH$_3$C=O); 1.47–3.76 (9H, m, H-cyclopentenyl, NCH$_2$); 1.13 (3H, t, J=7 Hz, CH$_3$CH$_2$).

EXAMPLE 107

$^1$H-NMR (CDCl$_3$) δ7.05–7.61 (4H, m, aryl-H); 4.92 (2H, s, broad, CH$_2$-7 ring); 2.69 (3H, s, CH$_3$—C=N); 2.22) 6H, s, (CH$_3$)$_2$N); 1.53–3.35 (12H, m, cyclopentenyl-H, CH$_2$—CH$_2$; NH).

EXAMPLE 108

$^1$H-NMR (CDCl$_3$) δ7.22–7.58 (4H, m, aryl-H); 4.93 (2H, s, broad, CH$_2$-7 ring); 3.67 (4H, m, CH$_2$O-morpholinyl); 2.67 (3H, s, CH$_3$C=N); 2.41 (4H, m, N—CH$_2$ morpholinyl); 1.51–3.30 (12H, m, NCH$_2$CH$_2$N, cyclopentenyl-H, NH).

EXAMPLE 109

$^1$H-NMR (CDCl$_3$ δ7.18–7.60 (4H, m, aryl-H); 4.94 (2H, s, broad, CH$_2$-7 ring); 2.70 (3H, s, CH$_3$C=N); 2.25 (6H, s, (CH$_3$)$_2$—N); 2.12 (3H, s, CH$_3$C=O); 1.16–3.79 (11H, m, H-cyclopentenyl, NCH$_2$CH$_2$N).

EXAMPLE 110

$^1$H-NMR (CDCl$_3$) δ7.17–7.61 (4H, m, aryl-H); 4.95 (2H, s, broad, CH$_2$-7 ring); 3.71 (4H, m, OCH$_2$ morphinyl-H); 2.69 (3H, s, CH$_3$C=N); 2.45 (4H, m, NCH$_2$-morpholinyl); 2.10 (3H, s, CH$_3$C=O); 1.47–3.56 11H, m, cyclopentenyl-H, NCH$_2$CH$_2$N).

EXAMPLE 111

$^1$H-NMR (CDCl$_3$) δ7.17–7.60 (4H, m, aryl-H); 4.94 (2H, s, broad, CH$_2$-7 ring); 2.69 (3H, s, CH$_3$C=N); 1.46–3.25 (16H, m, CH$_2$-cyclopentenyl, CH$_2$-piperidine, NH).

EXAMPLE 112

$^1$H-NMR (CDCl$_3$) δ7.10–7.59 (4H, m, aryl-H); 6.89 (1H, qu, J=<2 Hz, CH=); 4.90 (2H, s, broad, CH$_2$-7 ring); 3.98 (2H, d, J=6 Hz, OCH$_2$); 2.45 (3H, d, J=<2 Hz, CH$_3$—C=C); 2.03 (3H, s, CH$_3$—C=O); 1.59–3.35 (5H, m, cyclopentenyl-H).

EXAMPLE 113

$^1$H-NMR (CDCl$_3$) δ7.23–7.61 (4H, m, aryl-H); 6.90 (1H, qu, J=<2 Hz, CH=); 4.82 (2H, s, broad, 7-ring-CH$_2$); 3.66 (4H, m, OCH$_2$ morpholinyl); 2.44 (3H, d, J=<2 Hz, CH$_3$—C=C); 2.37 (4H, m, NCH$_2$-morpholinyl); 1.46–3.26 (7H, m, cyclopentenyl H).

EXAMPLE 114

$^1$H-NMR (CDCl$_3$) δ7.20–7.59 (4H, m, aryl-H); 6.88 ($^1$H, qu, J=<2 Hz, CH=); 4.78 (2H, s, broad, 7-ring-CH$_2$); 2.47 (4H, 2qu, J=7 Hz, N—(CH$_2$CH$_3$)$_2$); 2.45 (3H, d, J=<2 Hz, CH$_3$C=C); 1.55–3.15 (7H, m, H-cyclopentenyl); 0.93 (6H, t, J=Hz, N—(CH$_2$CH$_3$)$_2$).

EXAMPLE 115

$^1$H-NMR (CDCl$_3$) δ8.23 ($^1$H, s, NH-indole); 6.97–7.75 (9H, m, aryl; indolyl-H); 4.90 (2H, s, broad, 7-ring CH$_2$); 2.93 (4H, s, NCH$_2$CH$_2$N); 2.68 (3H, s, CH$_3$C=N); 1.49–3.10 (8H, m, cyclopentenyl-H, NH).

EXAMPLE 116

$^1$H-NMR (CDCl$_3$) δ7.23–7.60 (4H, m, aryl-H); 4.96 (2H, s, broad, CH$_2$-7 ring); 3.31 (3H, s, OCH$_3$); 3.30 (2H, d, J=6 Hz, OCH$_2$); 2.70 (3H, s, CH$_3$C=N); 1.56–3.39 (5H, m, cyclopentenyl-H).

EXAMPLE 117

$^1$H-NMR (CDCl$_3$) δ6.71–7.61 (9H, m, aryl-H); 4.95 (2H, s, broad, CH$_2$-7 ring); 3.90 OCH$_2$); 2.72 (3H, s, CH$_3$C=N); 1.58–3.40 (5H, m, cyclopentenyl-H).

EXAMPLE 125

$^1$H-NMR DMSO-d6(δ8.48 (1H, s, broad, CH=), 7.41–7.62 (4H, m, aryl-H); 5.00 (2H, s, broad, CH$_2$-7 ring); 3.16–3.26 (2H, m, CH$_2$—S); 2.63 (3H, s, CH$_3$—C=N), 1.40–3.16 (5H, m, H-cyclopentenyl); NH not visible.

EXAMPLE 126

$^1$H-NMR (CDCl$_3$) δ7.22–7.62 (4H, m, aryl-H); 4.93 (2H, s, broad, CH$_2$-7 ring); 3.42 (2H, d, J=10 Hz, CH$_2$Br); 2.70 (3H, s, CH$_3$—C=N); 1.64–3.33 (5H, m, H-cyclopentenyl)

EXAMPLE 127

$^1$H-NMR (CDCl$_3$) δ7.34–7.63 (4H, m, aryl-H); 4.92 (2H, s, broad, CH$_2$-7 ring); 2.74 (3H, s, CH$_3$C=N); 2.47 (2H, d, J=8 Hz, CH$_2$C=N); 1.61–3.32 (5H, m, H-cyclopentenyl).

EXAMPLE 130

$^1$H-NMR (CDCl$_3$): δ7.10–7.61 (m, 4H-aryl; 5.56/4.24 (AB system, J$_{AB}$=12 Hz, 2H, CH$_2$-7 ring); 3.52–3.93 (m, 4H, —OCH$_2$ morpholine); 2.68 (s, 3H, CH$_3$-triazole ring); 2.25–2.55 (m, 4H, N—CH$_2$ morpholine); 1.07–3.20 (m, 9H, CH$_2$, CH, 6-ring, N—CH$_2$).

EXAMPLE 131

$^1$H-NMR (CDCl$_3$): δ7.15–7.62 (m, 4H-aryl); 5.56/4.17 (AB system, J$_{AB}$=12 Hz, 2H, CH$_2$-7 ring); 3.59 (d, 2H, J=6 Hz, CH$_2$O); 2.66 (s, 3H, CH$_3$-triazole ring); 1.06–3.12 (m, 8H, CH$_2$, CH6-ring, N—CH$_2$)

EXAMPLE 133

$^1$H-NMR (CDCl$_3$) δ7.18–7.72 (4H, m, aryl-H); 6.89 (1H, qu, J=<2 Hz, CH=); 4.80–6.00 (6H, m, CH$_2$=CH—); 5.39/4.10 (2H, AB-syst. J$_{AB}$=12 Hz, CH$_2$-7 ring); 3.73–4.01 (4H, m, NCH$_2$); 3.50–3.73 (1H, m, cyclohexenyl-H); 2.41 (3H, d, J=<2 Hz, CH$_3$C=C); 1.58–2.00 (6H, m, CH$_2$-cyclohexenyl).

EXAMPLE 134

$^1$H-NMR (CDCl$_3$) δ7.11–7.64 (4H, m, aryl-H); 6.90 (1H, qu, J=<2 Hz, CH=); 5.42/4.12 (2H, AB-syst., J$_{AB}$=12 Hz, CH$_2$-7 ring); 2.42 (3H, d, J=<2 Hz, CH$_3$—C=C); 1.08–3.48 (15H, m, cyclohexenyl-H, N—(CH$_2$CH$_2$—)$_2$); 0.83 (6H, 2t, J=7 Hz, (CH$_2$CH$_2$CH$_3$)$_2$.

EXAMPLE 135

$^1$H-NMR (CDl$_3$) δ7.20–7.60 (4H, m, aryl-H); 4.80–5.97 (6H, m, CH$_2$=CH—); 4.21/5.17 (2H, AB-syst. J$_{AB}$=12 Hz, CH$_2$-7 ring); 3.54–4.01 (5H, m, CH$_2$N; CH-cyclohexenyl); 2.67 (3HC=N); 1.56–3.04 (6H, m, CH$_2$-cyclohexenyl).

EXAMPLE. 138

$^1$H-NMR (CDCl$_3$) δ7.21–7.56 (4H, m, aryl-H); 4.67–6.09 (6H, m, CH$_2$=CH); 4.89 (2H, s, broad, CH$_2$-7 ring); 1.89–4.13 (9H, m, NCH$_2$; cyclopentenyl-H); 2.68 (3H, s, CH$_3$—C=N).

EXAMPLE 139

$^1$H-NMR (CDCl$_3$) δ7.33–7.55 (4H, m, aryl-H); 4.92 (2H, s, broad, CH$_2$-7 ring); 2.74 (3H, s, CH$_3$C=N); 1.04–3.81 (33H, m, octylamine-CH$_2$, cyclopentenyl-H); 0.89 (6H, 2t, J=6 Hz, CH$_3$-cyclooctyl).

EXAMPLE 140

$^1$H-NMR (CDCl$_3$) δ7.22–7.58 (4H, m, aryl-H); 4.94 (2H, s, broad, CH$_2$-7 ring); 2.69 (3H, s, CH$_3$C=N); 1.23–3.41 (13H, m, N—CH$_2$CH$_2$—CH$_3$); 0.82 (6H, t, J=7 Hz, N—CH$_2$CH$_2$CH$_3$).

EXAMPLE 141

$^1$H-NMR (CDCl$_3$) δ7.22–7.56 (4H, m, aryl-H); 6.91 (1H, qu, J=<2 Hz, CH=); 4.80 (2H, s, broad, CH$_2$-ring); 1.22–3.93 (13H, m, N—CH$_2$CH$_2$—CH$_3$, cyclopentenyl-H); 2.43 (3H, d, J=<2 Hz, CH$_3$C=C); 0.84 (6H, t, J=7 Hz, N—CH$_2$CH$_2$CH$_3$).

EXAMPLE 142

$^1$H-NMR (CDCl$_3$) δ7.19–7.51 (4H, m, aryl-H); 6.88 (1H, qu, J=<2 Hz, CH=); 4.90–5.99 (6H, m, CH$_2$=CH); 4.70 (2H, s, broad, CH$_2$-7 ring); 1.81–4.06 (9H, m, NCH$_2$, cyclopentenyl-H); 2.42 (3H, d, J=<2 Hz, CH$_3$—C=C).

EXAMPLE 143

$^1$H-NMR (CDCl$_3$) δ7.28–7.54 (4H, m, aryl-H); 7.28; 7.20 (2H, 2d, J=<2 Hz, CH=CH); 4.98; 4.82 (2H, AB system, J$_{AB}$=15 Hz, CH$_2$-7 ring); 1.93–3.93 (13H, m, cyclopentenyl-H, morpholine-H).

EXAMPLE 144

$^1$H-NMR (CDCl$_3$) δ7.20–7.53 (4H, m, aryl-H); 5.22 (2H, s, broad, CH$_2$-7 ring); 2.25 (3H, s, CH$_3$—C=C); 1.86–3.87 (13H, m, cyclopentenyl-H, morpholine-H).

EXAMPLE 145

$^1$H-NMR (CDCl$_3$) δ7.18–7.53 (4H, m, aryl-H); 7.00 ($^1$H, qu, J=<2 Hz, CH=); 4.83 (2H, s, broad, CH$_2$-7 ring); 1.91–3.87 (13H, m, cyclopentenyl-H, morpholine-H; 2.26 (3H, d, J=<2 Hz, CH$_3$—C=C).

EXAMPLE 147

$^1$H-NMR (CDCl$_3$) δ7.26–7.53 (4H, m, aryl-H); 5.96 ($^1$H, t, J=7 Hz, NH); 4.86 (2H, s, broad, CH$_2$-7 ring); 2.71 (3H, s, CH$_3$ C=N); 1.39–3.43 (7H, m, cyclopentenyl-H, NCH$_2$); 1.26 (28H, s, hexadecanyl); 0.88 (3H, t, J=6 Hz, 3H, CH$_3$-hexadecanyl).

The following are Examples of some pharmaceutical compositions using compounds of general formula I or II as active ingredient. Unless expressly stated otherwise, the parts given are parts by weight.

Tablets

1. A tablet contains the following ingredients:

| | |
|---|---|
| Active substance of formula Ia/Ib | 0.020 parts |
| Stearic acid | 0.010 parts |
| Dextrose | 1.890 parts |
| Total | 1.920 parts |

Preparation:

The substances are mixed together in known manner and the mixture is compressed to form tablets each weighing 1.92 g and containing 20 mg of active substance.

2. Ointment

The ointment consists of the following ingredients:

| | |
|---|---|
| Active substance of formula Ia/Ib | 50 mg |
| Neribas ointment (commercial product of Scherax) | ad 10 g |

Preparation:

The active substance is triturated with 0.5 g of ointment base and the remaining base is added gradually in quantities of 1.0 g and intimately mixed to form an ointment. A 0.5% ointment is obtained. The distribution of the active substance in the base is monitored visually under a microscope.

3. Cream

Composition:

| | |
|---|---|
| Active substance of formula Ia/Ib | 50 mg |
| Neribas ointment (commercial product of Scherax) | ad 10 g |

Preparation

The active substance is triturated with 0.5 g of cream base and the remaining base is gradually incorporated with a pestle in quantities of 1.0 g. A 0.5% cream is obtained. The distribution of the active substance in the base is monitored visually under a microscope.

4. Ampoule solution

Composition:

| | |
|---|---|
| Active substance of formula Ia/Ib | 1.0 mg |
| Sodium chloride | 45.0 mg |
| Water for injection | ad 5.0 ml |

Preparation:

The active substance is dissolved in water at its own pH or optionally at pH 5.5 to 6.5 and sodium chloride is added to render the solution isotonic. The resulting solution is filtered free from pyrogens and the filtrate is transferred under aseptic conditions into ampoules which are then sterilised and fused to seal them. The ampoules contain 1 mg, 5 mg and 10 mg of active substance.

5. Suppositories

Each suppository contains:

| | |
|---|---|
| Active substance of formula Ia/Ib | 1.0 parts |
| Cocoa butter (m.p. 36–37° C.) | 1200.0 parts |
| Carnauba wax | 5.0 parts |

Preparation

Cocoa butter and carnauba wax are melted together. At 45° C. the active substance is added and stirred in until completely dispersed. The mixture is poured into suitably sized moulds and the suppositories are conveniently packaged.

6. Solutions for inhalation

Composition:

| | |
|---|---|
| a) Active substance of formula Ia/Ib | 500 mg |
| Na EDTA | 50 mg |
| Benzalkonium chloride | 25 mg |
| Sodium chloride | 880 mg |
| Distilled water ad | 100 ml |

Preparation:

96% of the water is put in first, then the Na EDTA, benzalkonium chloride, sodium chloride and active substance are dissolved therein and topped up with the remaining water. The solution is transferred to 20 ml dropper vials. One dose (20 drops, 1 ml) contains 5 mg of active substance.

| | |
|---|---|
| b) Active substance of formula Ia/Ib | 500 mg |
| Sodium chloride | 820 mg |
| Distilled water ad | 100 ml |

Preparation

96% of the quantity of water is put in, then the active substance and sodium chloride are dissolved therein, topped up with the remaining water and the solution is transferred into single dose containers (4 ml). The solution contains 20 mg of active substance.

What is claimed is:

1. A compound of the formula Ia or Ib

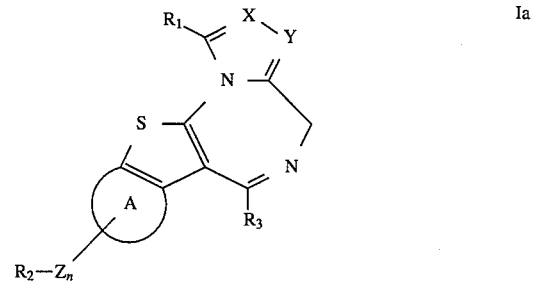

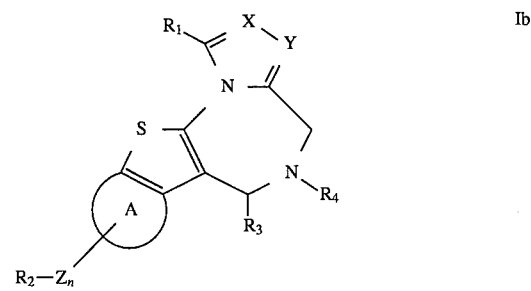

wherein

A is a fused mono-unsaturated 5-, 6- or 7-membered carbocyclic ring;

Z is a branched or unbranched alkyl or alkenyl group with n carbon atoms;

$R_1$ is hydrogen, lower alkyl, substituted lower alkyl, cycloalkyl, lower alkoxy, substituted lower alkoxy, or halogen;

$R_2$ is hydroxy, halogen, cyano, formyl, carboxy, alkyloxycarbonyl, aryloxycarbonyl, alkyl- or aryloxycarbonylalkyloxy, alkylsulphonyloxy, arylsulphonyloxy, alkyl- or arylsulphonylamino, amino, aminocarbonyl, aminocarbonylamino, alkoxycarbonylamino, aryloxycarbonylamino, aminocarbonyloxy, an amidine, an imido group, a C-linked $\Delta^2$-imidazoline, -thiazoline, -oxazoline, or tetrahydropyrimidine group which may optionally be mono- or polysubstituted by methyl, ethyl or isopropyl, a tetrahydropyrimidine ring, optionally mono or polysubstituted by methyl, a benzimidazole group, an indole group, hydrogen where n is greater than 0, an alkyl ether, a phenyl ether, or an alkylthio ether, $R_3$ is phenyl wherein the phenyl ring may be mono- or polysubstituted by methyl, halogen, nitro or trifluoromethyl; or pyridyl;

$R_4$ is hydrogen, alkyl or alkylcarbonyl;

X and Y independently of each other are N; and n is 0,1,2,3,4,5, or 6, or a pharmaceutically acceptable salt thereof.

2. The compound of the formula Ia according to claim 1, wherein A is a fused mono-unsaturated 5 or 6 membered carbocyclic ring Z is an unbranched alkyl group with n carbon atoms n is 0,1,2,3,or 4;

X and Y independently of each other are N;

$R_1$ is hydrogen, hydroxymethyl, chloromethyl, cyclopropyl, ethyl, methyl, methoxy, ethoxy, chlorine or bromine;

$R_2$ is hydroxy, amino, carboxy, cyano, bromine, alkoxycarbonyl with 1 to 6 carbon atoms, a group of the formula

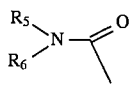

wherein $R_5$ and $R_6$, which may be identical or different, are hydrogen, a branched or unbranched alkyl group or alkenyl group with 1 to 6, 8 or 16 carbon atoms which may optionally be substituted by halogen, hydroxy, methoxy, nitro, amino, alkylamino or dialkylamino with 1 to 4 carbon atoms in the alkyl chain, or when $R_6$ is hydrogen or alkyl it may be substituted by morpholinylcarbonyl or diethylaminocarbonyl, when $R_5$ is hydrogen or methyl, $R_6$ is a thiazoline or thiazole group which may optionally be substituted by a branched or unbranched alkyl group with 1 to 4 carbon atoms, or $R_5$ and $R_6$, together with the nitrogen atom between them form a morpholino- or piperazino group which may optionally be mono- or polysubstituted by methyl;

$R_2$ is a C-linked $\Delta^2$-imidazoline, -thiazoline, -oxazoline, or tetrahydropyrimidine group which may optionally be mono- or polysubstituted by alkyl with 1 to 4 carbon atoms, or

wherein $R_8$ is an alkyloxycarbonyl group with 1 to 4 carbon atoms;

when n is greater than 0

$R_2$ is an alkylcarbonyloxy group with 1 to 3 carbon atoms;

$R_2$ is an alkylsulphonyloxy group with 1 to 2 carbon atoms;

wherein $R_7$ and $R_8$, which may be identical or different, are hydrogen, a branched or unbranched alkyl group with 1 to 6 carbon atoms, optionally substituted by dialkylamino with 1 to 4 carbon atoms, morpholino or N-alkylpiperazino or an indole group, or an alkylcarbonyl group with 1 to 4 carbon atoms, or $R_7$ and $R_8$, together with the nitrogen atom form a morpholino or piperazino group which may optionally be mono or polysubstituted by methyl, or a triazolo group, an imidazolo group, a pyrazolo group, a pyrrolo group or an imido group, $R_2$ is a branched or unbranched alkylsulphonyloxy group with 1 to 4 carbon atoms, a branched or unbranched alkylcarbonyloxy group with 1 to 8 carbon atoms;

$R_2$ is phenyloxy, 3,4-methylenedioxyphenoxy, a pyridinyloxy group, an alkyloxy or alkylthio group with 1 to 4 carbon atoms; and $R_3$ is phenyl or o-chlorophenyl; or a pharmaceutically acceptable salt thereof.

3. The compound of formula Ia, according to claim 1, wherein A represents a mono-unsaturated 5 or 6 membered ring;

Z is an unbranched alkyl group with n carbon atoms n is 0, 1, or 2;

X and Y both are N;

$R_1$ is hydrogen, methyl, cyclopropyl, methoxy, or bromine;

$R_2$ is hydroxy, amino, carboxy, cyano, methoxycarbonyl, ethoxycarbonyl, a group of the formula

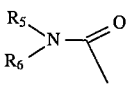

wherein $R_5$ and $R_6$, which may be identical or different, are hydrogen, a branched or unbranched alkyl group with 1 to 6, 8 or 16 carbon atoms, which may optionally be substituted by halogen, hydroxy, nitro, amino, ethylamino or diethylamino, methoxy or if $R_6$ is hydrogen or alkyl, it may be substituted by morpholinylcarbonyl or diethylaminocarbonyl, propenyl, or phenyl, if $R_5$ is hydrogen or methyl, $R_6$ is a thiazoline or thiazole group which may optionally be substituted by methyl, or $R_5$ and $R_6$ together with the nitrogen atom form a morpholino or piperazino group which may optionally be mono or polysubstituted by methyl;

$R_2$ is a C-linked $\Delta^2$-imidazoline, -thiazoline or -oxazoline group which may optionally be mono or polysubstituted by methyl, ethyl or, isopropyl, a tetrahydropyrimidine ring, optionally mono or polysubstituted by methyl, a benzimidazole group, or an indole group, $R_2$ when n is 0, is hydrogen, or methoxycarbonylamino;

when n is greater than 0

$R_2$ is an acetoxy group, a methanesulfonyloxygroup,

wherein $R_7$ and $R_8$, which may be identical or different, are hydrogen, a branched or unbranched alkyl group with 1 to 4 carbon atoms which may be substituted by diethylamino or morpholino, or an acetyl group or $R_7$ and $R_8$ together with the nitrogen atom form a morpholino or peperazino group which may optionally be mono or polysubstituted by methyl, or a triazolo group, an imidazolo group or a phthalimide, $R_2$ is a branched or unbranched alkylsulphonyloxy group with 1 to 4 carbon atoms, a branched or unbranched alkylcarbonyloxy group with 1 to 8 carbon atoms;

$R_2$ is a phenyloxy group, a pyridyloxy group, 3,4-methylenedioxyphenoxy, a 1,2,4-triazol-3-yl-thio group, methoxy, and $R_3$ is phenyl; or a pharmaceutically acceptable salt thereof.

4. The compound of formula Ia or Ib, according to claim 1, 2 or 3 wherein A is a 6-membered ring and the group $-Z_n-R_2$ is substituted in the 3 or 4 position of the hetrazepine.

5. The compound of formula Ia or Ib, according to claim 1, 2 or 3 wherein A is a 5-membered ring and the group $-Z_n-R_2$ is substituted in the 3-position of the hetrazepine.

6. The compound of formula Ia or Ib, according to claim 1, wherein A is a fused mono-unsaturated 5-, 6- or 7-membered carbocyclic ring, $R_1$, is hydrogen or methyl, $R_3$ is 2-chlorophenyl, and Z is $-CH_2-$ or a single bond.

7. 3-(Morpholin-4-yl-carbonyl)-5-(2-chlorophenyl)-10-methyl-3,4-dihydro-2H,7H-cyclopenta[4,5]thieno[3,2-f][1,2,4]triazolo[4,3-a][1,4]diazepine.

8. A method for treating pathological conditions and diseases in which PAF (platelet activating factor) is implicated, which comprises administering to a patient in need of such treatment a therapeutic amount of a compound of claim 1.

9. (−)-3-(Morpholin-4-yl-carbonyl)-5-(2-chlorophenyl)-10-methyl-3,4-dihydro-2H,7H-cyclopenta[4,5]thieno[3,2-f][1,2,4]triazolo[4,3-a][1,4]diazepine.

10. 3-(Dipropylaminocarbonyl)-5-(2-chlorophenyl)-10-methyl- 3,4-dihydro-2H,7H-cyclopental[4,5]thieno[3,2-f][1,2,4]triazolo[4,3-a][1,4]diazepine.

11. The compound according to claim 1, wherein A is a fused mono-unsaturated 5- or 6-membered carbocyclic ring.

12. The compound according to claim 1, 2 or 3, wherein A is a fused mono-unsaturated 5-membered carbocyclic ring.

* * * * *